United States Patent [19]

Egbertson et al.

[11] Patent Number: 5,204,350
[45] Date of Patent: Apr. 20, 1993

[54] METHOD OF INHIBITING OSTEOCLAST-MEDIATED BONE RESORPTION BY ADMINISTRATION OF N-HETEROCYCLICALKYL-SUBSTITUTED PHENYL DERIVATIVES

[75] Inventors: Melissa S. Egbertson, Ambler; George D. Hartman, Lansdale; Robert J. Gould, Green Lane, all of Pa.

[73] Assignee: Merck & Co., Inc., Rahway, N.J.

[21] Appl. No.: 742,970

[22] Filed: Aug. 9, 1991

[51] Int. Cl.$^5$ .................. A61N 31/495; A61N 31/40
[52] U.S. Cl. .................................... 514/255; 514/408; 514/835
[58] Field of Search .............. 514/255, 315, 567, 408

[56] References Cited

PUBLICATIONS

Journal of Cell Biology, vol. 111 (1990) by Sato, et al.
Journal of Bone and Mineral Research, vol. 5 No. 1, pp. 31–40 (1990), Sato et al.
Bone, 9 73–79 (1988), Kanasha, et al.

Primary Examiner—Frederick E. Waddell
Assistant Examiner—T. J. Criares
Attorney, Agent, or Firm—Charles M. Caruso; Frank P. Grassler; Richard S. Parr

[57] ABSTRACT

Compounds of the general formula

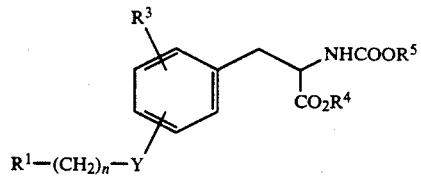

Y is an integer of from 0 to 6 is chosen from:
O,
$SO_2$,
—CONH—,
—NHCO—,
—$CH_2$— or

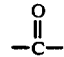

$R^1$ is substituted or unsubstituted mono- or polycyclic saturated hetero-cyclic ring system having 1, 2 or 3 heteroatoms where said heteroatoms are independently chosen from N, O and S and said substituents are chosen from the group comprising $R^2$;
$R^2$ is
$C_{1-6}$ alkyl,
aryl $C_{0-6}$alkyl,
hydroxy $C_{0-6}$alkyl,
$C_{1-6}$ alkoxy $C_{0-6}$alkyl,
carboxy $C_{0-6}$alkyl
oxo,
halogen,
$CF_3$,
$C_{0-4}$alkylamino-$C_{0-6}$alkyl or
$C_{0-4}$dialkylamino-$C_{0-6}$alkyl;
$R^3$ is
$C_{1-8}$ alkyl or cycloalkyl,
aryl $C_{0-4}$alkyl,
hydroxy $C_{0-4}$alkyl
$C_{1-4}$alkyloxy $C_{0-4}$alkyl,
carboxy $C_{0-4}$alkyl,
halogen,
$CF_3$ or
hydrogen;
$R^4$ is
hydrogen,
$C_{1-6}$alkyl,
aryl $C_{0-4}$alkyl or
$C_{1-6}$alkylcarbonyloxymethyl; and
$R^5$ is
$C_{1-6}$alkyl,
aryl $C_{0-4}$alkyl or
heterocycly $C_{0-4}$alkyl and the pharmaceutically acceptable salts thereof; are used in a method of treating osteoporosis by inhibiting the bone resorption activity of osteoclasts.

3 Claims, 1 Drawing Sheet

METHOD OF INHIBITING OSTEOCLAST-MEDIATED BONE RESORPTION BY ADMINISTRATION OF N-HETEROCYCLICALKYL-SUBSTITUTED PHENYL DERIVATIVES

BACKGROUND OF THE INVENTION

This invention relates to a new method for inhibiting bone resorption that is mediated by the action of a class of cells known as osteoclasts, involving compounds that compete with osteoclasts for the osteoclast' site of activity.

Osteoclasts are multinucleated cells of up to 400 μm in diameter that resorb mineralized tissue (chiefly, calcium carbonate and calcium phosphate) in vertebrates. They are actively motile cells that migrate along the surface of bone. They can bind to bone, secrete necessary acids and proteases and thereby cause the actual resorption of mineralized tissue from the bone.

In the method of the present invention, N-heterocyclicalkyl-substituted phenyl derivatives are administered in a pharmacologically effective amount that blocks osteoclasts from initiating bone resorption. These compounds have the general structural formula

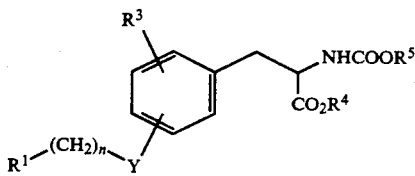

wherein
n is an integer of from 0 to 6;
Y is chosen from O, $SO_2$, —CONH, —NHCO—, $CH_2$ or

$R^1$ is an unsubstituted or substituted saturated mono- or polycyclic hetero-cyclic ring system having 1, 2 or 3 heteroatoms where said heteroatoms are chosen from O, N or S and wherein said substituents are independently chosen from $R^2$;
$R^2$ is
$C_{1-6}$ alkyl,
aryl $C_{0-6}$ alkyl,
hydroxy $C_{0-6}$ alkyl,
$C_{1-4}$ alkyloxy $C_{0-6}$ alkyl,
carboxy $C_{0-6}$ alkyl,
oxo,
halogen,
$CF_3$,
$C_{0-4}$ alkylamino $C_{0-6}$ alkyl or
$C_{0-4}$ dialkylamino $C_{0-6}$ alkyl;
$R^3$ is
hydrogen,
$C_{1-6}$ alkyl,
hydroxy $C_{0-4}$ alkyl,
$C_{1-4}$ alkyloxy $C_{0-4}$ alkyl,
carboxy $C_{0-4}$ alkyl,
halogen or
$CF_3$;
$R^4$ is
hydrogen,
$C_{1-6}$ alkyl,
aryl $C_{0-4}$ alkyl,
$C_{1-6}$ alkylcarbonyloxymethyl; and
$R^5$ is
$C_{1-6}$ alkyl,
aryl $C_{0-4}$ alkyl or
heterocyclyl $C_{0-4}$ alkyl,
and the pharmaceutically acceptable salts thereof.

A preferred group of compounds of the present invention are those defined for the general structural formula shown below wherein:

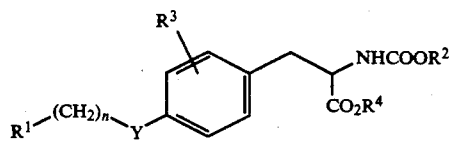

n is an integer from 0 to 6,
Y is chosen from
O,
—NHCO—,
—CONH— or
$CH_2$;
$R^1$ is an unsubstituted or substituted 5 or 6-membered heterocyclic ring system having 1, 2 or 3 heteroatoms where said heteroatoms are independently chosen from N or O and wherein said substituents are $C_{1-6}$ alkyl, aryl $C_{1-3}$ alkyl, hydroxy, $C_{1-4}$ alkoxy or oxo;
$R^2$ and $R^3$ are independently
hydrogen,
$C_{1-6}$ alkyl,
aryl $C_{0-4}$ alkyl,
hydroxy $C_{0-2}$ alkyl,
$C_{1-4}$ alkoxy $C_{0-2}$ alkyl,
carboxy $C_{0-3}$ alkyl or
oxo;
$R^4$ is
H or
$C_{1-4}$ alkyl,
and the pharmaceutically acceptable salts thereof.

A more preferred group of compounds of the present invention are those adjusted for the general structural formula shown below wherein:

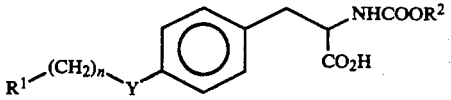

n is an integer of from 1 to 6;
Y is chosen from:
O, —NHCO—, —CONH— or $CH_2$;
$R^1$ is an unsubstituted or substituted 5 or 6-membered heterocyclic ring having 1 or 2 heteroatoms where said heteroatom is N and wherein said substituents are $C_{1-3}$ alkyl, hydroxy or oxo; and
$R^2$ is
$C_{1-6}$ alkyl or
aryl $C_{0-4}$ alkyl,
and the pharmaceutically acceptable salts thereof.

The pharmacologic activity of these compounds is useful in the treatment of poultry and mammals, including man.

The current major bone diseases of public concern are osteoporosis, hypercalcemia of malignancy, osteopenia due to bone metastases, periodontal disease, hyperparathyroidism, periarticular erosions in rheumatoid arthritis, Paget's disease, immobilization-induced osteopenia, and glucocorticoid treatment.

All these conditions are characterized by bone loss, resulting from an imbalance between bone resorption (breakdown) and bone formation, which continues throughout life at the rate of about 14% per year on the average. However, the rate of bone turnover differs from site to site, for example it is higher in the trabecular bone of the vertebrae and the alveolar bone in the jaws than in the cortices of the long bones. The potential for bone loss is directly related to turnover and can amount to over 5% per year in vertebrae immediately following menopause, a condition which leads to increased fracture risk.

There are currently 20 million people with detectable fractures of the vertebrae due to osteoporosis in the U.S. In addition, there are 250,000 hip fractures per year attributed to osteoporosis, which are associated with a 12% mortality rate within the first two years and 30% of the patients require nursing home care after the fracture.

All the conditions listed above would benefit from treatment with agents which inhibit bone resorption.

SUMMARY OF THE INVENTION

By this invention there is provided a process for the treatment of mammals suffering from a bone condition caused or mediated by increased bone resorption, who are in need of such therapy, comprising the step of administering a pharmacologically effective amount of a compound of formula I, including the pharmaceutically acceptable salts thereof, to inhibit the activity of mammalian osteoclasts.

DETAILED DESCRIPTION OF THE INVENTION

Figure 1:
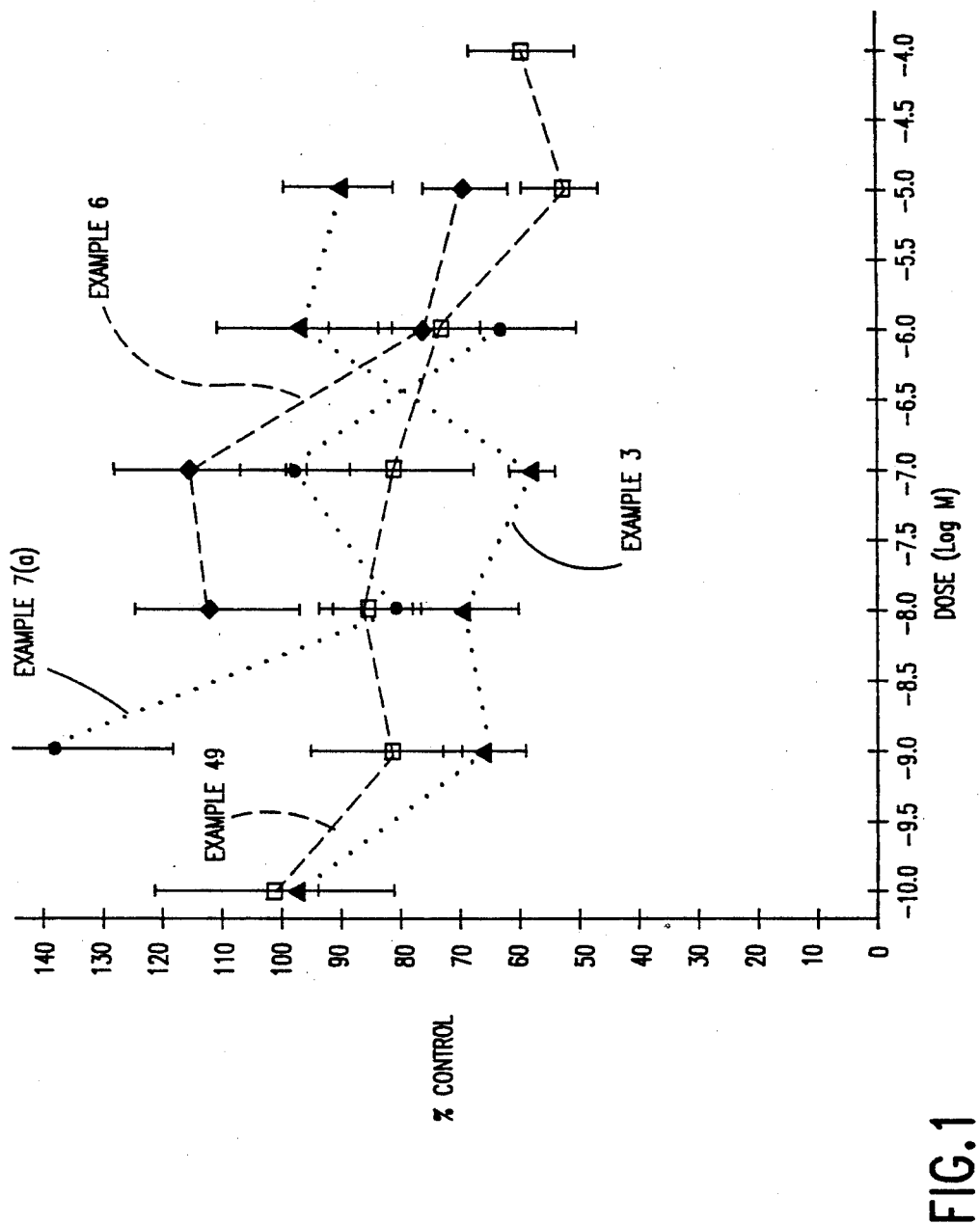
FIG. 1 illustrates the number of resorption pits formed by osteoclasts plotted as a function of concentration of the compound of interest.

The term "pharmaceutically acceptable salts" shall mean non-toxic salts of the compounds of this invention which are generally prepared by reacting the free base with a suitable organic or inorganic acid. Representative salts include the following salts:
Acetate
Benzenesulfonate
Benzoate
Bicarbonate
Bisulfate
Bitartrate
Borate
Bromide
Calcium Edetate
Camsylate
Carbonate
Chloride
Clavulanate
Citrate
Dihydrochloride
Edetate
Edisylate
Estolate
Esylate
Fumarate
Gluceptate
Gluconate
Glutamate
Glycollylarsanilate
Hexylresorcinate
Hydrabamine
Hydrobromide
Hydrochloride
Hydroxynapthoate
Iodide
Isothionate
Lactate
Lactobionate
Laurate
Malate
Maleate
Mandelate
Mesylate
Methylbromide
Methylnitrate
Methylsulfate
Mucate
Napsylate
Nitrate
Oleate
Oxalate
Pamaote
Palmitate
Pantothenate
Phosphate/diphosphate
Polygalacturonate
Salicylate
Stearate
Subacetate
Succinate
Tannate
Tartrate
Teoclate
Tosylate
Triethiodide
Valerate Additionally included are suitable cations such as alkali metal and alkaline earth cations.

The term "pharmacologically effective amount" shall mean that amount of a drug or pharmaceutical agent that will elicit the biological or medical response of a tissue, system or animal that is being sought by a researcher or clinician.

The term "bone resorption activity" shall mean the process by which osteoclasts solubilize bone minerals and increase the activity of enzymes that degrade bone matrix.

The term "alkyl" shall mean straight or branched chain alkane, alkene or alkyne with one or more degrees of unsaturation at any position.

In the schemes and examples below, various reagent symbols have the following meanings:

The term "oxo" shall mean

The term "heterocyclyl" shall mean a 5 or 6-membered mono or polycyclic ring system containing 1, 2, 3 or 4 heteroatoms chosen from O, N or S.

The term "halogen" shall mean F, Cl, Br or I.
The term "aryl" shall mean phenyl or benzyl.
BOC: t-butoxycarbonyl
Pd-C: Palladium on activated carbon catalyst.
DMF: Dimethylformamide
DMSO: Dimethylsulfoxide
CBZ: Carbobenzyloxy
EtOAc: ethyl acetate
THF: tetrahydrofuran
HOAc: acetic acid
$CHCl_3$: chloroform
MeOH: methanol
$CH_3CN$: acetonitrile
TFA: Trifluoroacetic acid
BOP: Benzotriazol-4-yloxy-tris(dimethylamino)-phosphonium hexaflurorphosphate The compounds of the present invention can be administered in such oral dosage forms as tablets, capsules (each of which includes sustained release or timed release formulations), pills, powders, granules, elixers, tinctures, suspensions, syrups and emulsions. Likewise, they may also be administered in intravenous (bolus or infusion), intraperitoneal, subcutaneous or intramuscular form, all using forms well known to those of ordinary skill in the pharmaceutical arts.

The dosage regimen utilizing the compounds of the present invention is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter or arrest the progress of the condition.

Oral dosages of the present invention, when used for the indicated effects, will range between about 0.01 mg per kg of body weight per day (mg/kg/day) to about 100 mg/kg/day and preferably 1.0-100 mg/kg/day and most preferably 1.0 to 20 mg/kg/day. Intravenously, the most preferred doses will range from about 1 to about 10 mg/kg/minute during a constant rate infusion. Advantageously, compounds of the present invention may be administered in a single daily dose, or the total daily dosage may be administered in divided doses of two, three or four times daily. Furthermore, preferred compounds for the present invention can be administered in intranasal form via topical use of suitable intranasal vehicles, or via transdermal routes, using those forms of transdermal skin patches well known to those of ordinary skill in that art. To be administered in the form of a transdermal delivery system, the dosage administration will, of course, be continuous rather than intermittant throughout the dosage regimen.

In the methods of the present invention, the compounds herein described in detail can form the active ingredient, and are typically administered in admixture with suitable pharmaceutical diluents, excipients or carriers (collectively referred to herein as 'carrier' materials) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water and the like. Moreover, when desired or necessary, suitable binders, lubricants, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

The compounds of the present invention can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

Compounds of the present invention may also be delivered by the use of monoclonal antibodies as individual carriers to which the compound molecules are coupled. The compounds of the present invention may also be coupled with soluble polymers as targetable drug carriers. Such polymers can include polyvinylpyrrolidone, pyran copolymer, polyhydroxypropylmethacrylamidephenol, polyhydroxyethylaspartamidephenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and crosslinked or amphipathic block copolymers of hydrogels.

The novel compounds used in the method of the present invention were prepared according to the procedure of the following schemes and examples, using appropriate materials and are further exemplified by the following specific examples. The most preferred compounds are any or all of those specifically set forth in these examples. These compounds are not, however, to be construed as forming the only genus that is considered as the invention, and any combination of the compounds or their moieties may itself form a genus. The following examples further illustrate details for the preparation of the compounds of the present invention. Those skilled in the art will readily understand that known variations of the conditions and processes of the following preparative procedures can be used to prepare these compounds. All temperatures are degrees Celsius unless otherwise noted.

SCHEME 1

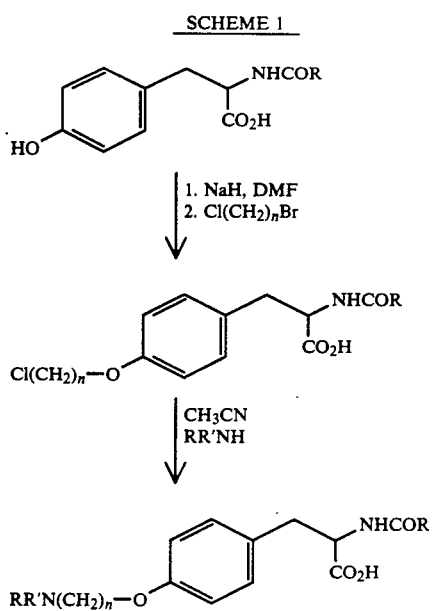

EXAMPLE 1

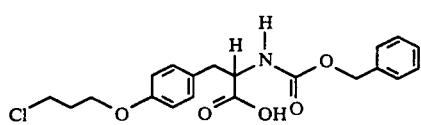

2-S-(N-Benzyloxycarbonylamino)-3-[4-(3-chloro-propyloxy)phenyl]propionic acid (1-1)

N-CBZ-tyrosine (3 g, 9.9 mmole) (Bachem Chemical Supply, California), was dissolved in DMF and treated with NaH (50% dispersion in oil, 0.95 g, 19.8 mmole) for 1 hour. Then 1,3-bromochloropropane (1 ml, 9.9 mmole) was added and the reaction stirred for 16 hours. The DMF was removed in vacuo and the residue dissolved in water, acidified to pH 3, and extracted with ethyl acetate. The ethyl acetate layer was dried with $MgSO_4$, filtered and evaporated. Column chromatography ($SiO_2$, 97:3:1 $CHCl_3/CH_3OH/HOAc$) yielded 1-1 as a yellow oil.

$R_f$=0.3 in 97:3:1 $CHCl_3/CH_3OH/HOAc$ ninhydrin stain $^1H$ NMR (300 MHz, $CDCl_3$) δ7.3 (bs, 5H), 7.03 (d, J=8.3, 2H), 6.8 (d, J=8.3, 2H), 5.2 (d, J=8 Hz, 1H), 5.05 (bs, 2H) 4.65 (m, 1H), 4.05 (t, J=5.7 Hz, 2H), 3.73 (t, J=6.3 Hz, 2H), 3.1 (m, 2H), 2.2 (m, 2H).

EXAMPLE 2

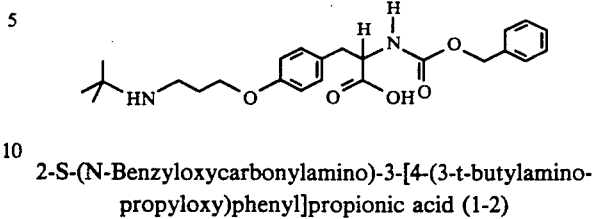

2-S-(N-Benzyloxycarbonylamino)-3-[4-(3-t-butylamino-propyloxy)phenyl]propionic acid (1-2)

Compound 1-1, 0.4 g, 1.1 mmole, was refluxed in t-butylamine (20 ml) and acetonitrile (20 mL) for three days. The reaction was evaporated to dryness, the residue dissolved in water, and extracted with ether. The aqueous layer was then acidified to pH 4–5 and a precipitate formed. The solid was collected and dried to yield 1-2.

Rf=0.8 in 9:1 $EtOH/NH_4OH$, ninhydrin stain.

300 MHz $^1H$ NMR ($D_2O$+NaOH) δ7.4 (bs, 2H), 7.2 (bs, 4H), 6.85 (d, J=8.55, 2H), 5.2 (d, J=12.8 Hz, 1H), 5.0 (d, J=12.8 Hz, 1H), 4.3 (dd, J=4.0, 9.6 Hz, 1H), 4.0 (bs, 2H), 3.2 (dd, J=4.0, 13.6 Hz, 1H), 2.8 (dd, J=9.6 Hz, 13.6 Hz, 1H), 2.65 (t, J=7.3 Hz, 2H), 1.8 (m, 2H), 1.09 (s, 9H), mass spec (FAB) m/e=429 (m+1)

C, H, N analysis $C_{24}H_{32}N_2O_5$ 0.65 $H_2O$ MW=440.244 Calculated C=65.47, H=7.62, N=6.36; Found: C=65.52, H=7.54, N=6.27.

EXAMPLE 3

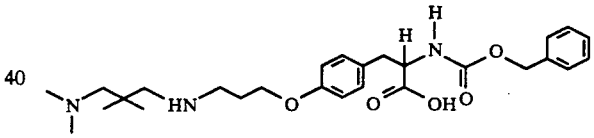

2-S-(N-Benzyloxycarbonylamino)-3-[4-(N,N,2,2-tetramethylpropanediamino)propyloxyphenyl]propionic acid (1-3)

Treatment of compound 1-1 with N,N,2,2-tetramethyl-1,3-propenediamine by refluxing in acetonitrile for three days, and followed by an aqueous workup provided crude 1-3. This was chromatographed on silica gel eluting with 9:1:1 $EtOH/H_2O/NH_4OH$ to provide pure 1-3 (Rf=0.37 ninhydrin stain). 300 MHz $^1H$ NMR ($D_2O$) δ7.5 (bs, 3H), 7.4 (bs, 2H), 7.33 (d, J=8.3 Hz, 2H), 7.0 (d, J=8.3 Hz, 2H), 5.20 (d, J=10 Hz, 1H), 5.10 (d, J=10 Hz, 1H), 4.25 (m, 1H), 4.25 (t, J=5.6 Hz, 2H), 3.4 (t, J=7.8 Hz, 2H), 3.4 (s, 2H), 3.25-2.95 (m, 2H), 3.22 (s, 2H), 3.1 (s, 6H), 2.35 (m, 2H), 1.38 (s, 6H).

MW=759.28

C, H, N analysis for $C_{27}H_{39}N_2O_5$ 2.4 $CF_3CO_2H$. Calcd: C, 50.30; H, 5.50; N, 5.53. Found: C, 50.35; H, 5.43; N, 5.56.

EXAMPLE 4

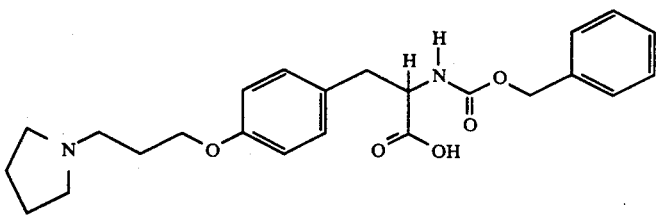

2-S-(N-Benzyloxycarbonylamino)-3-[4-(3-N-pyrolidinylpropyloxy)phenyl]propionic acid (1-4)

Treatment of compound 1-1 with pyrrolidine in CH$_3$CN at reflux for three days provided crude 1-4. This was purified by flash chromatography on silica gel eluting with 9:1:1 EtOH/H$_2$O/NH$_4$OH to give pure 1-4 (R$_f$=0.81, ninhydrin stain).

$^1$H NMR (300 MHz, CDCl$_3$) δ7.3 (bs, 5H), 7.0 (d, J=8.1 Hz, 2H), 6.7 (d, J=8.1 Hz, 2H), 5.5 (d, J=7.4 Hz, 1H), 5.0 (bs, 2H), 4.5 (m, 1H), 3.8 (m, 2H), 3.75 (bs, 1H), 3.4 (m, 2H), 3.18 (t, J=8.5 Hz, 2H), 3.1 (bs, 2H), 2.8 (bs, 1H), 2.2–1.8 (m, 6H).

C, H, N analysis C$_{24}$H$_{30}$N$_2$O$_5$·0.25CH$_2$Cl$_2$. Calcd: C, 65.05; H, 6.87; N, 6.26. Found: C, 65.28; H, 6.78; N, 6.27.

EXAMPLE 5

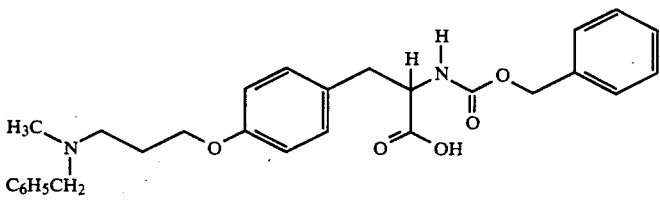

2-S-(N-Benzyloxycarbonylamino)-3-[4-(3-N-methyl-N-benzylaminopropyloxyphenyl)propionic acid (1-5)

Treatment of 1-1 with N-methyl benzylamine in acetonitrile at reflux for three days afforded crude 1-5. The solvent was removed on a rotary evaporator and the residue was dissolved in water and extracted with 3×75 mL portions of ether. The product separated out an oil which was collected and concentrated to give 1-5, after trituration with EtOAc and CH$_2$Cl$_2$ as a foam.

300 MHz $^1$H NMR (CDCl$_3$/CD$_3$OD) δ7.4 (m, 10H), 7.0 (d, J=8.5 Hz, 2H), 6.6 (d, J=8.5 Hz, 2H), 5.0 (bs, 2H), 4.5 (m, 1H), 4.2 (bs, 2H), 3.88 (t, J=5.3 Hz, 2H), 3.1–2.8 (m, 4H), 2.69 (s, 3H), 2.2 (bs, 2H).

C, H, N analysis C$_{28}$H$_{32}$N$_2$O$_5$·0.8CH$_2$Cl$_2$·0.25 EtOAc Calcd: C, 63.17; H, 6.33; N, 4.94. Found: C, 63.16; H, 6.40; N, 5.04.
MW=548.771

EXAMPLE 6

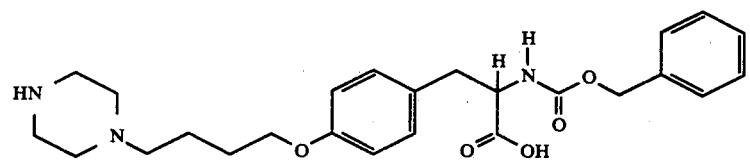

2-S-(N-t-Butyloxycarbonylamino)-3-[4-(3-N-t-butylpropyloxy)phenyl]propionic acid (1-6)

Treatment of N-BOC-L-tyrosine with sodium hydride in DMF followed by 1,3-bromochloropropane provided the N-BOC analog of 1-1. This was treated with an excess of t-butylamine in refluxing acetonitrile for two days to provide crude 1-6 after aqueous workup and extraction. Pure 1-6 was prepared by preparative reverse phase HPLC.

300 MHz $^1$H NMR (CD$_3$OD) δ7.17 (d, J=8.5 Hz, 2H), 6.85 (d, J=8.5 Hz, 2H), 4.28 (dd, J=4.8, 9.1 Hz, 1H), 4.1 (t, J=5.9 Hz, 2H), 3.2 (t, J=7.7 Hz, 2H), 3.1 (dd, J=4.8, 13.3 Hz, 1H), 2.8 (dd, J=9.1, 13.3 Hz, 1H), 2.15 (m, 2H), 1.38 (s, 18H).

C, H, N analysis C$_{21}$H$_{34}$N$_2$O$_7$·1.05CF$_3$CO$_2$H. MW=514.243. Calcd: C, 53.95; H, 6.87; N, 5.45. Found: C, 54.01; H, 6.97; N, 5.51.

EXAMPLE 7

2-S-(N-Benzyloxycarbonylamino)-3-[4-(4-piperazinyl)-butyloxyphenyl]propionic acid (1-7)

Treatment of N-CBZ-L-tyrosine with sodium hydride in DMF followed by 1,4-dibromobutane, as described for the preparation of 1-1, provided the corresponding butyl analog. Treatment of this with 1,4-piperazine in refluxing acetonitrile for three days gave crude 1-7 as a precipitate from the reaction mixture. Reverse phase HPLC purification gave pure 1-7.

$^1$H NMR (300 MHz, CD$_3$OD) δ7.3 (m, 5H), 7.23 (d, 2H), 6.83 (d, 2H), 5.0 (bs, 2H), 4.35 (dd, 1H), 4.0 (t, 2H), 3.6 (bs, 8H), 3.1 (dd, 1H), 2.85 (dd, 1H), 2.00–1.8 (m, 4H).

C, H, N analysis C$_{26}$H$_{35}$N$_3$O$_5$.1.2H$_2$O. MW = 491.206. Calcd: C, 63.57; H, 7.67; N, 8.56. Found: C, 63.33; H, 7.28; N, 8.55.

EXAMPLE 7(a)

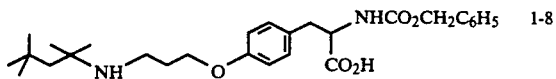

2-S-(N-Benzyloxycarbonylamino)-3-[4-(1,1,3,3-tetramethylbutylamino)propyloxyphenyl]pentanoic acid (1-8)

Treatment of 1-1 with 1,1,3,3-tetramethylbutylamine, as described for compound 1-2, gave 1-8 as the TFA salt.

$^1$H NMR (300 MHz CD$_3$OD) δ7.35 (5H, m), 7.18 (2H, d), 6.85 (1H, d), 5.00 (2H, s), 4.35 (1H, dd), 4.10 (2H, t), 3.1 (2H, t), 3.15 (1H, dd), 2.50 (1H, dd), 2.1 (2H, m), 1.70 (2H, s), 1.5 (6H, s), 1.10 (9H, s).

Analysis for C$_{28}$H$_{40}$N$_2$O$_5$.0.9CF$_3$CO$_2$H. Calcd: C, 60.94; H, 7.02; N, 4.77. Found: C, 60.85; H, 7.01; N, 4.69.

EXAMPLE 7(b)

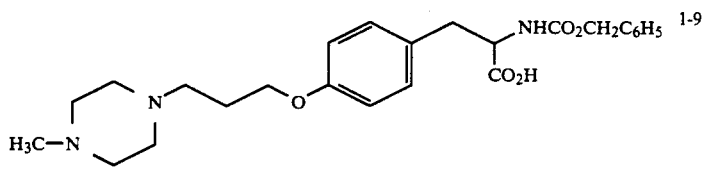

2-S-(N-Benzyloxycarbonyl)-3-[4-(4-methylpiperazin-1-yl)-propyloxyphenyl]propanoic acid (1-91)

Treatment of 1-1 with N-methylpiperazine as described for 1-2 gave crude 1-9. This was purified by column chromatography on silica gel eluting with 9:1:1 C$_2$H$_5$OH/H$_2$O/NH$_4$OH to give pure 1-9 as the TFA salt.

$^1$H NMR (300 MHz, D$_2$O) δ7.5 (3H, m), 7.4 (2H, d), 7.0 (2H, d), 5.18 (1H, d), 5.05 (1H, d), 4.5 (1H, m), 4.2 (2H, t), 3.8 (8H, s), 3.6 (2H, t), 3.3 (1H, m), 3.1 (3H, s), 3.0 (1H, m), 2.4 (2H, m).

Analysis for C$_{25}$H$_{33}$N$_3$O$_5$.2.3CF$_3$CO$_2$H. Calcd: C, 49.52; H, 4.96; N, 5.85. Found: C, 49.42; H, 4.98; N, 6.01.

EXAMPLE 7(c)

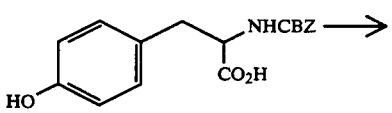

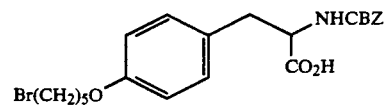

2-(N-Benzyloxycarbonylamino)-3-[4-(5-bromopentyloxy)phenyl]propionic acid (1-10)

N-CBZ-L-tyrosine (2.06 g, 5.86 mmole) was treated with NaH (0.58 g, 12.08 mmole) and 1,5-dibromopentane (0.8 ml, 5.87 mmole) as described for 1-1 in Example 1. The crude product was dissolved in methanol and after stirring with silica gel for 0.5 hour, the solvent was removed. This was dry packed and eluted on a flash column with CHCl$_3$ and then with 97:3:0.3 CHCl$_3$/CH$_3$OH/HOAc to give pure 1-10

$^1$H NMR (300 MHz, CD$_3$OD) δ1.50–1.65 (2H, m), 1.63–1.95 (4H, m), 3.10 (2H, m), 3.45 (1H, t), 3.92 (2H, m), 4.40 (1H, m), 6.80 (2H, d), 7.10 (2H, d), 7.28 (5H, m).

EXAMPLE 7(d)

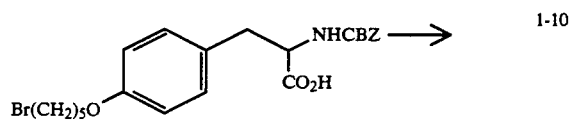

2-S-(N-Benzyloxycarbonylamino)-3-[4-(4-piperazin-1-yl)pentyloxyphenyl]propionic acid (1-11)

1-10 (0.658 g, 1.42 mmole), was dissolved in 30 mL CH$_3$CN and 1,4-piperazine (1.22 g, 14.16 mmole) was added. This solution was stirred at room temperature for 4 days. The solvent was then removed and the residue was dry packed on a silica gel column and eluted with 18:1:1 C$_2$H$_5$OH/H$_2$O/NH$_4$OH to give pure 1-11 as a white solid.

$^1$H NMR (300 MHz, CD$_3$OD) δ1.52 (4H, m), 1.77 (2H, m), 2.40 (2H, t), 2.59 (4H, m), 2.80–2.94 (1H, m), 3.01–3.12 (5H, m), 3.94 (2H, m), 4.21 (1H, m), 6.76 (2H, d), 7.09 (2H, d).

Analysis for C$_{26}$H$_{35}$N$_3$O$_5$.1.2 H$_2$O. Calcd: C, 63.57; H, 7.67; N, 8.56 Found: C, 63.33; H, 7.28; N, 8.55

SCHEME 2

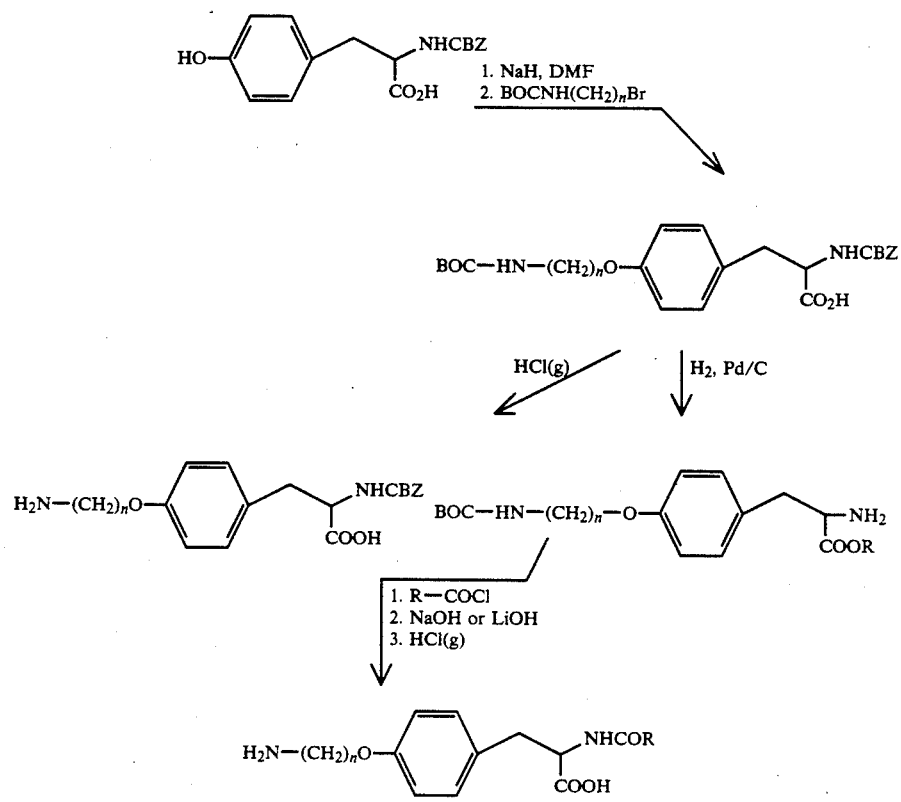

EXAMPLE 8

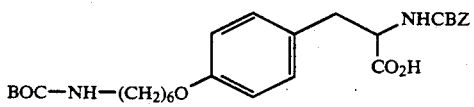

2-S-(N-Benzyloxycarbonylamino)-3-[4-(6-N-t-butyloxycarbonylaminohexyloxy)phenyl]propionic acid (2-1)

N-CBZ-L-tyrosine (15.0 g, 0.045 moles) was dissolved in 75 mL DMF and added at 0°-10° C. to a suspension of sodium hydride (2.16 g, 0.09 moles) in (-SOUTH-). The resulting suspension was stirred at 0°-10° C. for 1.0 hour and then 6-(N-t-butyloxycarbonylamino)hexyl bromide (12.6 g, 0.045 moles) in 25 mL DMF was added dropwise at 0°-5° C. and the clear, dark reaction mixture was stirred at room temperature overnight.

After solvent removal, the residue was taken up in EtOAc and this was made acidic with 10% KHSO$_4$ solution. The organic phase was separated, washed with brine, dried (Na$_2$SO$_4$) and the solvent removed to give an oil. This was purified by column chromatography on silica gel eluting with 98:2:1 CHCl$_3$/CH$_3$OH/HOAc to give pure 2-1 as a clear oil.

$^1$H NMR (300 MHz CD$_3$OD) δ1.45 (15H, m), 1.75 (2H, m), 2.80–3.15 (6H, m), 3.91 (2H, t), 4.38 (1H, m), 4.95 (6H, m), 6.79 (2H, d), 7.10 (2H, d), 7.28 (5H, m).

EXAMPLE 9

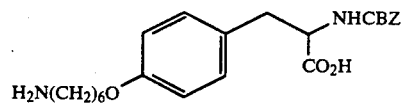

2-S-(N-Benzyloxycarbonylamino)-3-[4-(6-aminohexyloxyphenyl)]propionic acid hydrochloride (2-2)

Compound 2-1 (51.4 mg, 0.1 mmole) was dissolved in 20 mL EtOAc and cooled to −20° C. under N$_2$. HCl gas was bubbled into this solution for 10 minutes as the temperature rose to −5° C. The reaction mixture was stoppered and stirred at 0° to −5° C. for 1 hour. The solvent was then removed in the rotary evaporator and the residue was triturated with ether to give 2-2 as a white solid. Rf=0.4 (SiO$_2$, 9:1:1 EtOH/NH$_4$OH, H$_2$O).

$^1$H NMR (300 MHz, CD$_3$OD) δ1.45 (6H, m), 1.73 (4H, m), 2.90 (3H, m), 3.13 (1H, m), 3.95 (2H, m), 4.30 (1H, bs), 6.77 (2H, d), 7.10 (2H, d), 7.32 (4H, m).

Analysis for C$_{23}$H$_{31}$N$_2$O$_5$Cl.0.5 H$_2$O. Calcd: C, 60.05; H, 7.01; N, 6.09. Found: C, 60.08; H, 7.06; N, 6.09.

EXAMPLE 10

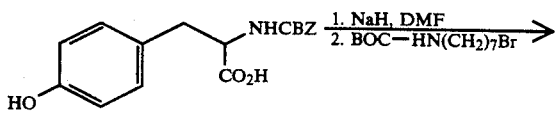

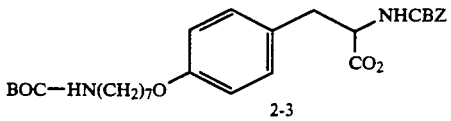

(2-3)

2-S-(N-Benzyloxycarbonylamino)-3-[4-(7-N-t-butyloxycarbonylaminoheptyloxy)phenyl]propionic acid (2-3)

N-CBZ-L-tyrosine (1.27 g, 4.02 mmoles) was alkylated with 7-(N-t-butyloxycarbonylaminoheptyl)bromide as taught in Example 8 for compound 2-1. Crude product was purified by flash chromatography on silica gel eluting with 95:5:0.5 $CHCl_3/CH_3OH/HOAc$ to give 2-3 as a clear oil.

$^1$H NMR (300 MHz $CD_3OD$) $\delta$1.40 (20H, m), 1.66 (2H, m), 2.82 (1H, m), 2.97–3.18 (4H, m), 3.91 (2H, m), 4.19 (1H, m) 5.0 (2H, q), 6.77 (2H, d), 7.10 (2H, d), 7.30 (5H, m).

EXAMPLE 11

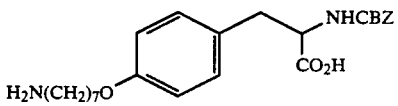

(2-4)

2-S-(N-Benzyloxycarbonylamino)-3-[4-(7-aminoheptyloxy)phenyl]propionic acid hydrochloride (2-4)

Compound 2-3 (67.4 mg, 0.127 mmole) was deprotected with HCl gas as described in Example 9 for 2-2 to provide pure 2-4.

$^1$H NMR (300 MHz $CD_3OD$) $\delta$1.32 (9H, m), 1.60 (4H, m), 2.77 (3H, m), 3.00 (1H, m), 3.18 (2H, m), 3.72 (2H, m), 4.25 (1H, m), 4.90 (2H, q), 6.70 (2H, d), 7.00 (2H, d), 7.18 (5H, m).

Analysis for $C_{24}H_{32}N_2O_5 \cdot 0.2EtOH \cdot 0.75 H_2O$. Calcd: C, 64.94; H, 7.75; N, 6.21. Found: C, 64.97; H, 7.84; N, 6.22.

EXAMPLE 12

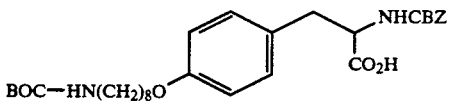

(2-5)

2-S-(N-Benzyloxycarbonylamino)-3-[4-(8-N-t-butyloxycarbonylaminooctyloxy)phenyl]propionic acid (2-5)

N-CBZ-L-tyrosine·$H_2O$ (1.5 g, 4.29 mmole) was dissolved in $EtOAc/CH_2Cl_2$, dried over $MgSO_4$, filtered and evaporated. The residue was dissolved in DMF and treated with NaH (50% dispersion in oil, 0.43 g, 8.96 mmole) for 1 hour. N-BOC-8-amino-1-bromooctane (1.33 g, 4.34 mmole) was added and the reaction was stirred for 16 hours. The DMF was removed in vacuo, the residue dissolved in water, acidified to pH 3 and extracted with EtOAc. The EtOAc layers were combined, dried and concentrated. Column chromatography ($SiO_2$, 97:3:1 $CHCl_3/MeOH/HOAc$) gave 2-5.

$^1$H NMR (300 MHz $CD_3OD$) $\delta$7.3 (m, 5H), 7.1 (d, 2H), 6.78 (d, 2H), 5.0 (2q, 2H), 4.38 dd, 1H), 3.8 (m, 2H), 3.13 (dd, 1H), 3.0 (t, 2H), 2.85 (dd, 1H), 1.75 (m, 2H), 1.4 (s, 9H), 1.35 (m, 3H), 1.3 (bs, 7H).

EXAMPLE 13

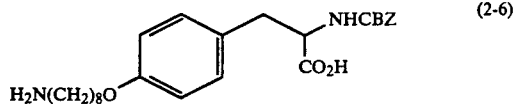

(2-6)

2-S-(N-Benzyloxycarbonylamino)-3-[4-(8-aminooctyloxy)phenyl]propionic acid (2-6)

Compound 2-5 (1.35 g, 2.49 mmole) was dissolved in ethyl acetate and treated with HCl gas at $-20°$ C., purged with $N_2$ and concentrated to give a white solid which was rinsed with ethyl acetate and dried to give 2-6.

$^1$H NMR (300 MHz $CD_3OD$) $\delta$7.3 (m, 5H), 7.1 (d, 2H), 6.8 (d, 2H), 5.02, (2q, 2H), 4.35 (dd, 1H), 4.93 (t, 2H), 3.1 (dd, 1H), 2.9 (t, 2H), 2.85 (dd, 1H), 1.75 (m, 2H), 1.65 (m, 2H), 1.5 (m, 2H), 1.4 (bs, 6H).

Analysis for $C_{25}H_{34}N_2O_5 \cdot HCl \cdot 0.65H_2O$. MW=490.732. Calcd: C, 61.18; H, 7.46; N, 5.71. Found: C, 61.18; H, 7.45; N, 5.77.

EXAMPLE 14

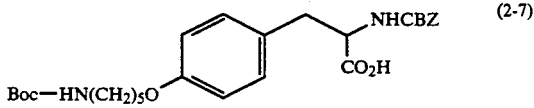

(2-7)

2-S-(N-Benzyloxycarbonylamino)-3-[4-(5-N-t-butyloxycarbonylaminopentyloxy)phenyl]propionic acid (2-7)

N-CBZ-L-tyrosine (1.06 g, 3.01 mmole) was alkylated with 5-(N-t-butyloxycarbonylamino)pentyl bromide as described for compound 2-1 in Example 8. Crude product was purified by flash chromatography on silica gel eluting with 97:3:0.5 $CHCl_3/CH_3OH/HOAc$ to give pure 2-7.

$^1$H NMR (300 MHz, $CD_3OD$) $\delta$1.42 (9H, S), 1.52 (4H, m), 1.76 (2H, m), 3.05, (3H, m), 3.92 (2H, t), 5.00 (2H, m), 6.79 (2H, d), 7.11 (2H, d), 7.28 (5H, m).

EXAMPLE 15

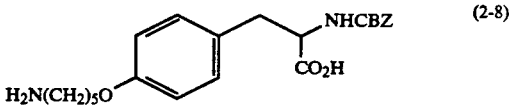

(2-8)

2-S-(N-Benzyloxycarbonylamino)-3-[4-(5-aminopentyloxy)phenyl]propionic acid hydrochloride (2-8)

2-7 was treated with HCl gas as taught in Example 9 for compound 2-2, to provide pure 2-8 as a white powder.

$^1$H NMR (300 MHz, $CD_3OD$) $\delta$1.60 (2H, m), 1.77 (4H, m), 2.90 (3H, m), 3.12 (1H, m), 3.96 (2H, t), 4.37 (1H, m), 5.02 (2H, m), 6.81 (2H, d), 7.12 (2H, d), 7.30 (5H, m).

Analysis for $C_{22}H_{29}N_2O_5 \cdot 0.25 H_2O$. Calcd: C, 59.85; H, 6.74; N, 6.35. Found: C, 59.85; H, 6.73; N, 6.32.

5,204,350

17

Scheme 3

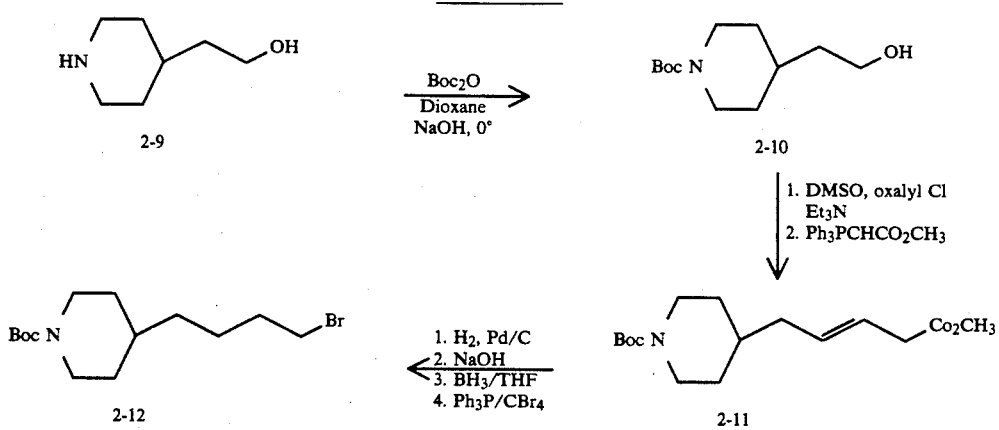

EXAMPLE 16

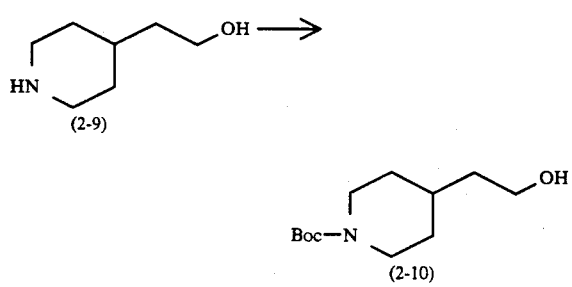

2-(4-N-t-Butyloxycarbonylpiperidin-4-yl)ethanol (2-10)

4-piperidine-2-ethanol (Available from Aldrich) (130 g, 1.0 mole) was dissolved in 700 mL dioxane, cooled to 0° C. and treated with 3 N NaOH (336 mL, 1.0 mole), and di-t-butylcarbonate (221.8 g, 1.0 mole). The ice bath was removed and the reaction stirred overnight. The reaction was concentrated, diluted with water and extracted with ether. The ether layers were combined, washed with brine, dried over MgSO$_4$, filtered and evaporated to give 2-10.

R$_f$=0.37 in 1:1 EtOAc/Hexanes, ninhydrin stain $^1$H NMR (300 MHz, CDCl$_3$) δ4.07 (bs, 2H), 3.7 (bs, 2H), 2.7 (t, J=12.5 Hz, 2H), 1.8-1.6 (m, 6H), 1.51 (s, 9H), 1.1 (ddd, J=4.3, 12.5, 12 Hz, 2H).

EXAMPLE 17

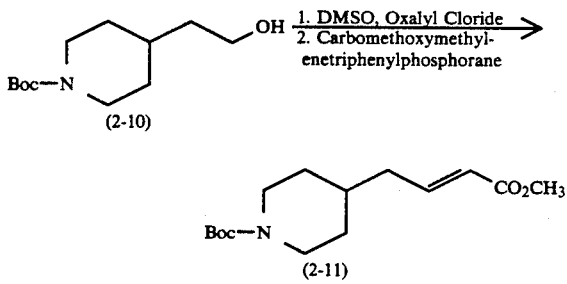

Methyl 4-(4-N-t-Butyloxycarbonylpiperidin-4-yl) but-2-enoate (2-11)

Oxalyl chloride (55.8 mL, 0.64 mole) was dissolved in 1 L CH$_2$Cl$_2$ and cooled to −78° C. under N$_2$. DMSO

18

(54.2 mL, 0.76 mole) was added dropwise. After gas evolution had ceased, 2-10 (102.5 g, 0.45 mole) dissolved in 200 mL CH$_2$Cl$_2$ was added over 20 minutes. After stirring an additional 20 minutes, triethylamine (213 mL, 1.53 mole) was added dropwise and the cold bath removed. After 1 and ½ hours TLC showed starting material gone. Carbomethoxytriphenylphosphorane (179 g, 0.536 mole) was added and the reaction stirred overnight. The solution was diluted with 300 mL Et$_2$O, extracted once with 800 mL H$_2$O, twice with 300 mL 10% KHSO$_4$ solution, then once with 300 mL brine. The organic layer was dried over MgSO$_4$, filtered and evaporated. Column chromatography (SiO$_2$, 5% EtOAc/Hexanes) yielded of pure 2-11.

$^1$H NMR (300 MHz, CDCl$_3$) δ6.9 (ddd J=15.6, 7,6, 7.6 Hz, 1H), 5.8 (d, J=15.6 Hz, 1H), 4.0 (bs, 2H), 3.7 (s, 3H), 2.6 (t, J=12.6 Hz, 2H), 2.1 (t, J=7.4 Hz, 2H), 1.7-1.4 (m, 3H), 1.4 (s, 9H), 1.1 (m, 2H).

EXAMPLE 18

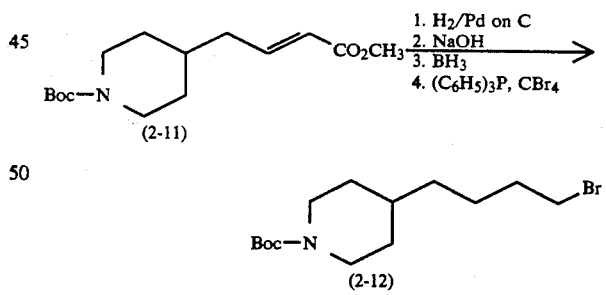

4-(4-N-t-Butyloxycarbonylpiperidin-4-yl)butyl bromide (2-12)

Compound 2-11 (36.2 g, 0.128 mole), was dissolved in 500 mL EtOAc. 10% Palladium on carbon (10 g) was added as a slurry in EtOAc and the reaction was placed under H$_2$ (in a balloon) overnight. The reaction was filtered through Solka-Floc, the cake washed with EtOAc and the ethyl acetate evaporated to give 4-(4-N-t-butyloxycarbonylpiperidin-4-yl)butanoate. TLC R$_f$=0.69 in 30% EtOAc/Hexanes.

$^1$H NMR (300 MHz, CDCl$_3$) δ4.0 (bs, 2H), 3.6 (s, 3H), 2.60 (t, J=12.3 Hz, 2H), 2.20 (t, J=7.4, 2H), 1.6 (m,

4H), 1.40 (s, 9H), 1.40 (m, 1H), 1.20 (m, 2H), 1.0 (m, 2H).

The butanoate ester (45.3 g, 0.159 mole) was dissolved in CH$_3$OH and treated with 1N NaOH (500 mL, 0.5 mole) overnight. The solvent was removed in vacuo, water was added and the solution washed with ether, then acidified with 10% KHSO$_4$ solution. The aqueous layer was washed with ether, the ether layers were combined, washed with brine and dried over MgSO$_4$ and concentrated to give the corresponding acid as a clear oil.

$^1$H NMR (300 MHz, CDCl$_3$) δ4.0 (bs, 2H), 2.6 (m, 2H), 2.25 (m, 2H), 1.6 (bs, 4H), 1.4 (s, 9H), 1.3–0.9 (9H).

This acid (20.4 g, 0.077 moles) was treated with borane (BH$_3$/THF, 235 mL, 235 mmole) in THF at 0° C. for 1 hour. NaOH (1N, 250 mL) was added dropwise and the solution stirred overnight. The reaction was concentrated to remove THF, extracted with ether, the ether extracts were combined, dried over MgSO$_4$, filtered and evaporated to give the corresponding alcohol as a colorless oil.

R$_f$=0.7 in 2:1 ethyl acetate/hexanes.

$^1$H NMR (300 MHz, CDCl$_3$) δ4.1 (bs, 2H), 3.6 (t, 2H), 2.65 (t, 2H), 2.1 (bs, 1H), 1.65 (bs, 2H), 1.55 (m, 2H), 1.4 (s, 9H), 1.35 (m, 3H), 1.25 (m, 2H), 1.1 (m, 2H).

This alcohol (19.7 g, 76.5 mmole) was dissolved in THF and treated with triphenylphosphine (23.1 g, 88 mmol) and cooled to 0° C. Carbon tetrabromide (29.8 g, 89.9 mmol) was added in one portion, the cold bath was removed and the reaction stirred overnight. Additional triphenylphosphine (11.71 g) and carbon tetrabromide (14.9 g) was added to drive the reaction to completion. The mixture was filtered and the liquid was diluted with ether and filtered again. After solvent removal the resulting liquid was adsorbed onto SiO$_2$ and chromatographed with 5% EtOAc/Hexanes to yield 2-12 as a clear colorless oil.

R$_f$=0.6 in 1:4 ethyl acetate/hexanes $^1$H NMR (300 MHz, CDCl$_3$) δ4.1 (bs, 2H), 3.4 (t, 2H), 2.65 (t, 2H), 1.85 (m, 2H), 1.65 (bd, 2H), 1.4 (s, 9H), 1.35 (m, 2H), 1.3 (m, 3H), 1.1 (m, 2H).

EXAMPLE 19

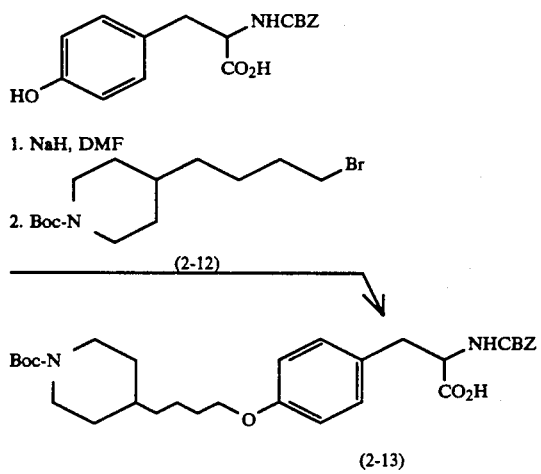

2-S-(N-Benzyloxycarbonylamino)-3-[4-(4-N-t-butyloxycarbonylpiperidin-4-ylbutyloxy) phenyl]propionic acid (2-13)

N-CBZ-L-tyrosine was alkylated with 2-12 as taught for compound 2-5 in Example 12 to provide 2-13.

R$_f$=0.15 in 97:3:1 CHCl$_3$/CH$_3$OH/HOAc, iodine stain.

$^1$H NMR (300 MHz, CDCl$_3$) δ7.2 (d, J=7.5 Hz, 2H), 7.1 (d, J=7.5 Hz, 2H), 7.0 (d, J=7.9 Hz, 2H), 6.8 (d, J=7.3 Hz, 2H), 5.2 (d, J=7.9 Hz, 1H), 5.1 (s, 2H), 4.6 (m, 1H), 4.01 (bd, 2H), 3.92 (t, J=6 Hz, 2H), 3.7 (m, 2H), 2.65 (bt, 7H), 1.75–1.4 (m, 7H), 1.45 (s, 9H), 1.3 (m, 2H), 1.1 (m, 2H).

EXAMPLE 20

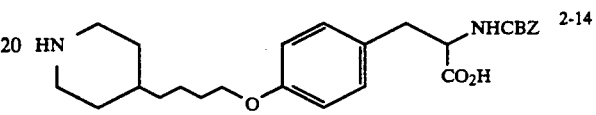

2-S-(N-Benzyloxycarbonylamino)-3-[4-(4-piperidin-4-ylbutyloxy)phenyl]propionic acid (2-14)

Compound 2-13 was deprotected as taught for compound 2-2 in Example 9. The solvent was removed on the rotary evaporator and the residue was dissolved in water and extracted with ethyl acetate. The water layer was concentrated to dryness, evaporated and the residue was chromatographed (SiO$_2$, 9:1:1 EtOH/H$_2$O/NH$_4$OH). A small portion was then purified further by HPLC and isolated as the TFA salt.

$^1$H NMR (300 MHz, CD$_3$OD) δ7.3 (m, 5H), 7.1 (d, 2H), 6.8 (d, 2H), 5.0 (q, 2H), 2.93 (t, 2H), 2.85 (dd, 1H), 1.92 (bd, 2H), 1.75 (m, 2H), 1.6–1.45 (m, 3H), 1.35 (m, 4H).

Mass Spec. (FAB) m/e=455 (m+1).

EXAMPLE 21

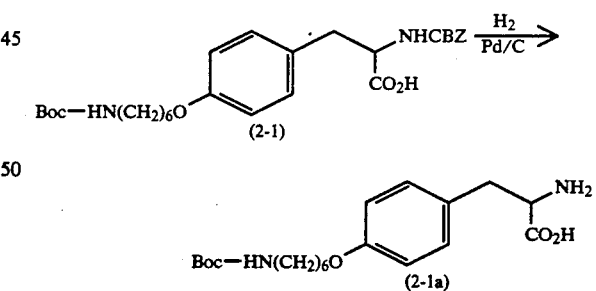

2-S-Amino-3-[4-(6-N-t-butyloxycarbonylaminohexyloxy)phenyl]propionic acid (2-1a)

A solution of compound 2-1 (0.52 g, 1.0 mmole) in 20 mL of 4:1 ethanol/HOAc was hydrogenated under balloon pressure for 8 hours. The catalyst was filtered off and the solvent removed on the rotary evaporator to give a residue that was triturated with 30 mL ether to provide 2-1a.

$^1$H NMR (300 MHz, CD$_3$OD) δ1.40 (9H, m), 1.75 (2H, m), 2.90–3.05 (3H, m), 3.10–3.23 (3H, m), 3.70 (1H, m), 3.96 (3H, t), 6.88 (2H, d), 7.20 (2H, d).

EXAMPLE 22

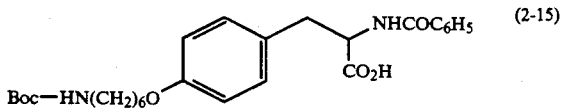

2-S-(Phenylcarbonylamino)-3[4-(6-N-t-butyloxycarbonylaminohexyloxy)phenyl] propionic acid (2-15)

0.152 g (0.4 mmole) of compound 2-1a was added to a solution of 1N NaOh (0.4 ml) in 10 mL H$_2$O and this was stirred at 0°–5° C. for 10 minutes as most of the solid dissolved. To this vigorously stirred suspension was added benzoyl chloride (0.062 g, 0.44 mmole) followed by solid sodium bicarbonate (0.037 g, 0.44 mmol) and the resulting mixture was stirred at 0°–5° C. for 1 hour.

The reaction mixture was then diluted with 30 mL H$_2$O and acidified to pH 2-3 with 10% KHSO$_4$ solution. This was extracted with 3×50 mL EtOAc and the combined organic extract was washed with 30 mL of H$_2$O, 30 mL of brine and dried (Na$_2$SO$_4$), Solvent removal provided a viscous residue that was purified by flash chromatography on silica gel eluting with chloroform(95)-methanol(5) to give 2-15 as a viscous residue.

$^1$H NMR (300 MHz, CDCl$_3$) δ1.40 (9H, m), 1.75 (2H, bs), 3.20 (m, 4H), 3.92 (2H, m), 5.03 (2H, m), 6.79 (2H, d), 7.10 (2H, d), 7.45 (3H, m), 7.72 (2H, m).

EXAMPLE 23

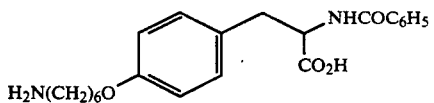

2-S-(Phenylcarbonylamino)-3-[4-(6-aminohexyloxy)-phenyl]propionic acid hydrochloride (2-16)

0.28 g (2.0 mmole) of compound 2-15 was dissolved in 20 mL of EtOAc and this was cooled to −15° C. and HCl gas was bubbled into the solution for 10 minutes. The resulting mixture was stoppered and stirred at 0° C. for 1.5 hours at which point all starting material was consumed. The solvent was then removed on the rotary evaporator to afford a white, foam-like residue. This was stirred with 30 mL ether for 1 hour and the resulting solid was collected by filtration to provide pure 2-16 as a white solid.

$^1$H NMR (300 MHz, CD$_3$OD) δ1.50 (3H, m), 1.70 (2H, m), 1.78 (2H, m), 2.90 (2H, t), 3.21 (4H, m), 3.94 (2H, t), 6.80 (2H, d), 7.19 (2H, d), 7.42 (2H, m), 7.50 (1H, m), 7.72 (2H, d).

Analysis for C$_{22}$H$_{38}$N$_2$O$_4$; HCl.0.75H$_2$O. Calc.: C=60.82, H=6.90, N=6.45. Found: C=60.89, H=6.67, N=6.35.

EXAMPLE 24

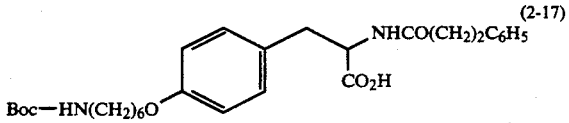

2-S-Phenethylcarbonylamino-3[4-(6-N-t-butyloxycarbonylaminohexyloxy)phenyl]propanoic acid (2-17)

To a solution of 1.2 mL 1N NaOH in 15 mL H$_2$O cooled to 0°–5° C. and stirred was added 0.457 g (1.2 mmole) of compound 2-14 and the resulting mixture was stirred for 10 minutes during which time most of the solid dissolved. To this vigorously stirred suspension was then added 3-phenylpropanoyl chloride (0.223 g, 1.32 mmole) followed by solid sodium carbonate (0.111 g, 1.32 mmole). The resulting white mixture was stirred vigorously at 0°–5° C. for 1.5 hours. The reaction mixture was then diluted with 40 mL H$_2$O and this was acidified to pH 2–3 with a 10% KHSO$_4$ solution. The resulting aqueous phase was then extracted with 4×50 mL portions of EtOAc, and the combined organic phase was washed with 50 mL H$_2$O, 50 mL brine and dried (Na$_2$SO$_4$). Solvent removal gave a viscous solid that was purified by flash chromatography on silica gel, eluting with chloroform (95)-methanol(5) to give of pure 2-17 as a clear viscous gum.

$^1$H NMR (300 MHz, CDCl$_3$) δ1.40 (9H, m), 1.72 (2H, bs), 2.50 (2H, m), 3.02 (6H,m), 3.91 (2H, m), 6.72 (2H, d), 6.88 (2H, m), 7.20 (3H, m), 7.29 (2H, m).

EXAMPLE 25

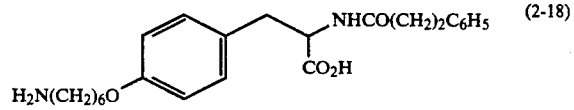

2-S-(Phenethylcarbonylamino)-3-[4-(6-aminohexyloxy)phenyl]propanoic acid hydrochloride (2-18)

A solution of compound 2-17 (0.3 g, 3.0 mmole) in 15 mL EtOAc was cooled to −15° C. and HCl gas was bubbled in for 10 minutes. The stoppered reaction mixture was then stirred for 2 hours at 0° C. at which time all 2-17 was consumed. The solvent was then removed on the rotary evaporator and the resulting foam was triturated with 40 mL ether at room temperature for 1.0 hour to give pure 2-18 as a white solid.

$^1$H NMR (300 MHz, CD$_3$OD) δ1.48 (3H, m), 1.67 (2H, m), 1.80 (2H, m), 2.46 (2H, m), 2.80 (3H, m), 2.90 (2H, m), 3.30 (3H, m), 3.95 (2H, t), 6.79 (2H, d), 7.06 (2H, d), 7.15 (3H, m), 7.22 (2H, m).

Analysis for C$_{24}$H$_{32}$N$_2$O$_4$.HCl.H$_2$O Calc.: C=61.72, H=7.55, N=6.00. Found: C=61.97, H=7.11, N=5.96.

EXAMPLE 26

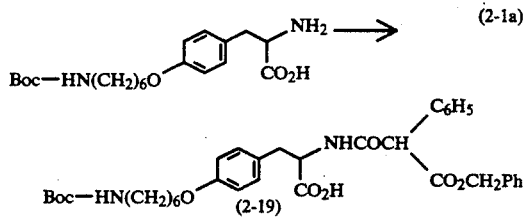

2-S-(2-Benzyloxycarbonyl)phenylacetylamino-3[4-(6-N-t-butyloxycarbonylaminohexyloxy)phenyl] propionic acid (2-19)

To a cold solution of 1.8 mL of 1 N NaOH in 15 mL H$_2$O was added 0.685 g (1.8 mmole) of compound 2-1a with stirring to give, after 10 minutes, a clear solution. Then, 2-benzyloxycarbonylphenylacetyl chloride (0.577 g, 2.0 mmole) was added followed by sodium bicarbonate (0.168 g, 2.0 mmole) and the resulting mixture was stirred at 0°–5° C. for 1.0 hour. The reaction mixture was diluted with water, acidified to pH 2–3 with 10% KHSO₄ solution and extracted with 4×500 mL portions of EtOAc. The combined organic extracts were washed with brine, dried (Na₂SO₄) and the solvent was removed to give a viscous amber residue. This was purified by column chromatography on silica gel, eluting with CHCl₃ (98)-methanol (2) to give pure 2-19 as an oil.

¹H NMR (300 MHz CDCl₃)δ1.45 (9H, 6s), 1.75 (2H, 6s), 3.07 (4H, m), 3.89 (2H, bs), 4.57 (2H, bs), 5.15 (2H, m), 6.69 (2H, d), 6.88 (2H, d), 7.30 (5H, m).

EXAMPLE 27

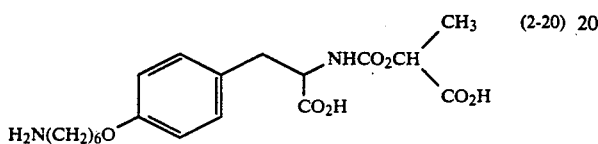

2-S-(2-Carboxyphenylacetylamino)-3-[4-(6-aminohexyloxy)phenyl]propionic acid hydrochloride (2-20)

Compound 2-19 (0.34 g, 0.55 mmole) was dissolved in 25 mL absolute ethanol and after adding 100 mg 10% Pd/C the suspension was hydrogenated under balloon pressure. Then, the catalyst was filtered off and the solvent removed on the rotary evaporator to give 0.25 g of 2-S-(2-Carboxyphenylacetylamino)-3-[4-(6-N-t-butyloxycarbonylaminohexyloxy)phenyl]-propionic acid.

¹H NMR (300 MHz, CD₃OD) δ1.47 (12H, m), 1.78 (2H, m), 3.06 (3H, m), 3.32 (4H, m), 3.92 (2H, m), 4.60 (2H, m), 6.72 (2H, d), 6.96, (2H, d), 7.30 (5H, m).

This acid was dissolved in 25 mL EtOAc and treated with HCl gas as described for compound 2-2 in Example 9. Solvent removal provided a residue that was purified by flash chromatography on silica gel eluting with 9:1:1 ethanol/H₂O/NH₄OH to give pure 2-20.

¹H NMR (300 MHz, D₂O) δ1.55 (H, m), 1.90 (2H, m), 2.83–3.09 (4H, m), 3.28 (1H, m), 4.15 (2H, m), 6.88–7.45 (9H, m).

Analysis for C₂₄H₃₀N₂O₆. 1.5 H₂O. 0.25 NH₃ Calc.: C=60.84, H=7.18, N=6.65. Found: C=60.48, H=6.81, N=6.99.

EXAMPLE 28

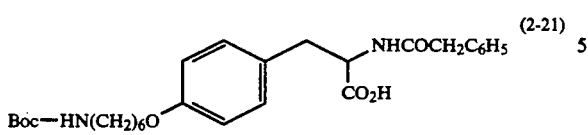

2-S-(Phenacylamino)-3-[4-(6-N-t-butyloxycarbonylaminooxy)phenyl]propionic acid (2-21)

Compound 2-1a (0.685 g, 1.8 mmole) was acylated with phenacyl chloride as described for compound 2-19 in Example 26. The crude product was purified by flash chromatography on silica gel eluting with 95:5:0.5 CHCl₃/CH₃OH/HOAc to give pure 2-21 as a viscous oil.

¹H NMR (300 MHz, CD₃OD) δ1.45 (12H, m), 1.78 (2H, m), 2.88 (1H, m), 3.10 (3H, m), 3.30 (1H, m), 3.48 (2H, m), 3.92 (2H, m), 4.61 (1H, m), 6.74 (2H, d), 7.02 (2H, d), 7.12 (2H, m) 7.22 (3H, m).

EXAMPLE 29

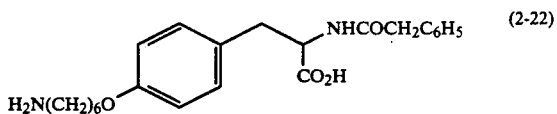

2-S-(Phenylacylamino)-3-[4-(6-aminohexyloxy)phenyl]propionic acid (2-22)

Compound 2-21 (0.35 g) was dissolved in 25 mL EtOAc and this solution was treated with HCl gas as described for compound 2-16 in Example 23 to give pure 2-22 as a white solid.

¹H NMR (300 MHz, CD₃OD) δ1.50 (6H, m), 1.65 (2H, m), 2.20 (2H, m), 2.88 (3H, m), 3.12 (1H, m), 3.30 (2H, m), 3.47 (2H, m), 3.94 (2H, m), 4.61 (1H, m), 6.75 (2H, d), 7.02 (2H, d), 7.13 (2H, d), 7.30 (3H, m).

Analysis for C₂₃H₃₀N₂O₄.HCl.H₂O Calc.: C=60.98, H=7.34, N=6.19. Found: C=61.29, H=6.92, N=6.12.

EXAMPLE 30

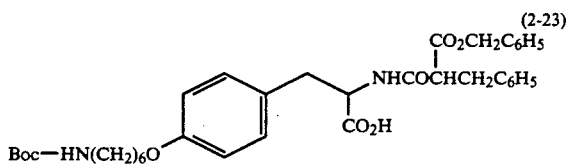

2-S-[(2-Benzyloxycarbonyl-3-phenylpropionylamino]-3-[4-(6-N-t-butyloxycarbonylaminohexyloxy)phenyl]propionicacid (2-23)

Compound 2-1a (0.685 g, 1.8 mmole) was acylated with 2-benzyloxycarbonyl-3-phenylpropionyl chloride as described for compound 2-19 in Example 26. The crude product was purified by flash chromatography on silica gel eluting with 98:2:1 CHCl₃/CH₃OH/HOAc to give pure 2-23 as a viscous oil.

¹H NMR (300 MHz, CD₃OD) δ1.40 (16H, m), 1.61 (2H, m), 3.03 (8H, m), 3.30 (6H, m), 3.71 (1H, m), 3.86 (2H, m), 4.60 (1H, m), 5.02 (2H, m), 6.70 (2H, d), 6.86, (1H, d), 7.02 (1H, 3), 7.22 (5H, m).

EXAMPLE 31

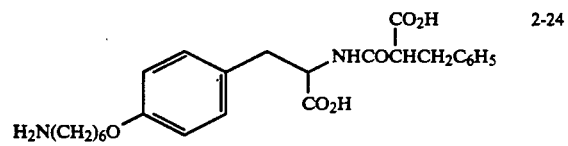

2-S-(2-Carboxy-3-phenylpropionylamino)-3-[4-(6-aminohexyloxy)phenyl]propionic acid (2-24)

Compound 2-23 (0.49 g, 0.76 mmole) was dissolved in 25 mL ethanol and after the addition of 100 mg 10% Pd/C hydrogenated at balloon pressure overnight. Solvent removal provided 2-S-(2-carboxy-3-phenylpropionylamino)-3-[4-(6-N-t-butyloxycarbonylaminooxy)phenyl]propionic acid as a viscous residue.

¹H NMR (300 MHz, CD₃OD) δ1.42 (10H, m), 1.75 (2H, m), 2.80–3.15 (5H, m), 3.30 (1H, m), 3.90 (2H, m), 4.58 (2H, m), 6.68–6.85 (4H, m), 7.06–7.27 (5H, m).

This acid (0.32 g) was treated with HCl gas as described above for compound 2-12 to give after solvent removal a crude product that was purified by flash chromatography on silica gel eluting with 90:5:5 CHCl₃/CH₃OH/HOAc to provide the diastereomeric products 2-24a and 2-24b.

2-24a had ¹H NMR (300 MHz, D₂O) δ1.58 (4H, m), 1.83 (4H, m), 2.95 (2H, m), 3.08 (3H, m), 3.20 (1H, m), 3.51 1H, m), 4.18 (2H, m), 4.53 (1H, m), 4.95 (2H, g), 6.92 (4H, m), 7.43 (5H, m).

2-24b had ¹H NMR (400 MHz, D₂O) δ1.40 (4H, m), 1.62 (2H, m), 1.73 (2H, m) 2.90 (6H, m), 3.31 (1H, m), 4.17 (2H, m), 4.32 (1H, m), 6.93 (2H, d), 7.07 (2H, d), 7.15 (2H, d), 7.26 (3H, m).

EXAMPLE 31(a)

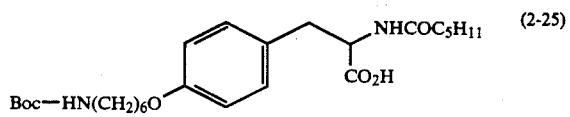

2-S-(Hexanoylamino)-3-[4-(6-N-t-butyloxycarbonylaminohexyloxy)phenyl]propionic acid (2-25)

(2-1a) (0.685 g, 1.8 mmole) was treated with hexanoyl chloride (0.38 g, 2.0 mmole) as described for 2-15 to provide crude 2-25. This was purified by flash chromatography on silica gel eluting with 95:5:1 CHCl₃/CH₃OH/HOAc to give pure 2-25 as an oil.

¹H NMR (300 MHz, CDCl₃) δ0.89 (3H, t), 1.20–1.65 (21H, m), 1.75 (2H, m), 2.19 (2H, t), 3.11 (4H, m), 3.92 (2H, m), 4.83 (1H, m), 6.80 (2H, d), 7.05 (2H, d).

EXAMPLE 31(b)

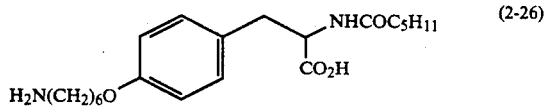

2-S-(Hexanoylamino)-3-[4-(6-aminohexyloxy)phenyl]-propionic acid hydrochloride (2-26)

2-25 (0.35 g, 0.75 mmole) was dissolved in 30 mL EtOAc and treated with HCl as described for compound 2-2 to give a foam-like solid that was triturated with 50 mL of ether for 1 hour at room temperature. This gave pure 2-26 as a white solid.

¹H NMR (300 MHz, CD₃OD) δ0.85 (3H, t), 1.20 (4H, m), 1.48 (6H, m), 1.68 (2H, m), 1.77 (2H, m), 2.14 (2H, m), 4.61 (1H, m), 6.80 (2H, d), 7.13 (2H, m).

Analysis for C₂₁H₃₄N₂O₄·HCl·0.5 H₂O. Calc: C=59.49, H=8.56, N=6.61. Found: C=59.32, H=8.48, N=6.55.

EXAMPLE 31(c)

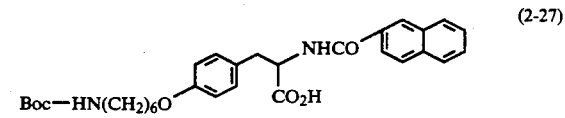

2-S-(2-Napthanoylamino)-3-[4-(6-N-t-butyloxycarbonylaminooxy)phenyl]propionic acid (2-27)

2-1a (0.685 g, 1.8 mmole) was treated with 2-napthanoyl chloride (0.409 g, 2.0 mmole) as described for 2-15 to provide crude 2-27. This was purified by flash chromatography on silica gel eluting with 95:4:1 CHCl₃/CH₃OH/HOAc to give pure 2-27 as a white solid. ¹H NMR (300 MHz, CD₃OD) δ1.45 (16H, m), 1.70 (2H, m), 2.88 (1H, m), 3.08 (3H, m), 3.57–3.80 (4H, m), 4.62 (1H, m), 6.54 (2H, d), 6.92 (2H, d), 7.25 (1H, d), 7.42 (2H, m), 7.61 (1H, bs), 7.77 (3H, m).

EXAMPLE 31(d)

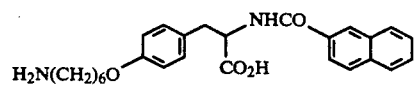

2-S-(Naphthanoylamino)-3-[4-(6-aminohexyloxy)-phenyl]propionic acid (2-28)

2-27 (0.14 g, 0.31 mmole) was dissolved in 25 mL EtOAc and treated with HCl gas as described for 2-2. Crude product was purified by flash chromatography on silica gel eluting with 10:1:1 C₂H₅OH/H₂O/NH₄OH to give pure 2-28 as a white solid.

¹H NMR (300 MHz, CD₃OD), δ1.42 (5H, m), 1.71 (2H, m), 2.63 (2H, m), 2.86 (1H, m), 3.07 (2H, m), 3.30 (3H, m), 3.55–3.75 (4H, m), 4.47 (1H, m), 6.43 (2H, d), 6.82 (2H, d), 7.30 (1H, dd), 7.45 (2H, m), 7.64 (1H, bs), 7.80 (3H, m).

Analysis for C₂₇H₃₂N₂O₄·0.5 H₂O. Calc: C=70.87, H=7.27, N=6.12. Found: C=70.93, H=7.04, N=6.11.

EXAMPLE 31(e)

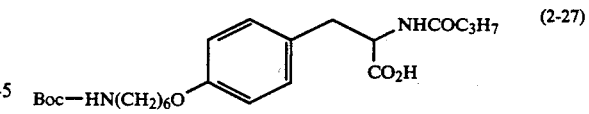

2-S-(2-Butanoylamino)-3-[4-(6-N-t-butyloxycarbonylaminohexyloxy)phenyl]propionic acid (2-29)

2-1a (0.685 g, 1.8 mmole) was acylated with butanoyl chloride as described for 2-15 to give crude 2-29. This was purified by flash chromatography eluting with 95:4:1 CHCl₃/CH₃OH/HOAc to provide pure 2-29 as an oil.

¹H NMR (300 MHz, CD₃OD) δ0.73 (3H, t), 1.32–1.60 (16H, m), 1.73 (2H, m), 2.12 (2H, m), 2.87 (1H, m), 3.03 (2H, t), 3.12 (1H, m), 3.92 (2H, t), 4.61 (1H, m), 6.80 (2H, d), 7.12 (2H, d).

EXAMPLE 31(f)

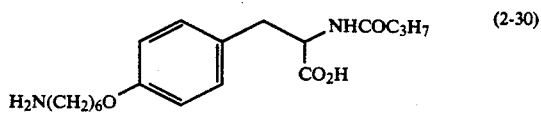

2-S-(Butanoylamino)-3-[4-(6-aminohexyloxy)phenyl]-propionic acid (2-30)

2-29 (0.05 g, 1.0 mmole) was dissolved in 25 mL ethyl acetate and treated with HCl gas as described for 2-2. Crude reaction product was triturated with 25 mL ether to give pure 2-30 as a white solid.

$^1$H NMR (300 MHz, CD$_3$OD) δ0.72 (3H, t), 1.45–1.60(6H, m), 1.70 (2H, m), 1.79 (2H, m), 2.12 (2H, m), 2.80–2.95 (3H, m), 3.14 (1H, dd), 3.30 (1H, m), 3.95 (2H, t), 4.40 (1H, m), 6.80 (2H, d), 7.13 (2H, d).

Analysis for C$_{19}$H$_{30}$N$_2$O$_4$.HCl.H$_2$O. Calc.: C=56.35, H=8.21, N=6.92. Found: C=56.70, H=8.12, N=6.91.

EXAMPLE 31(g)

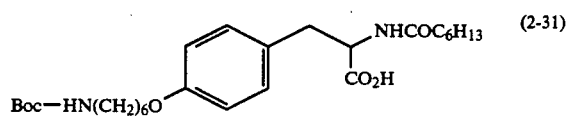
(2-31)

2-S-(Heptanoylamino)-3-[4-(6-N-t-butyloxycarbonylaminooxy)phenyl]propionic acid (2-31)

2-1a (0.685 g, 1.8 mmole) was acylated with heptanoyl chloride as described for 2-15. Crude product was purified by flash chromatography on silica gel eluting with 96:3:1 CHCl$_3$/CH$_3$OH/HOAc to give pure 2-31 as an oil.

$^1$H NMR (300 MHz, CD$_3$OD) δ0.78 (3H, t), 1.22 (6H, m), 1.32–1.55 (16H, m), 1.73 (2H, m), 2.13 (2H, m), 2.85 (1H, m), 3.02 (2H, t), 3.15 (1H, m), 4.91 (2H, t), 4.61 (1H, m), 6.81 (2H, d), 7.12 (2H, d).

EXAMPLE 31(h)

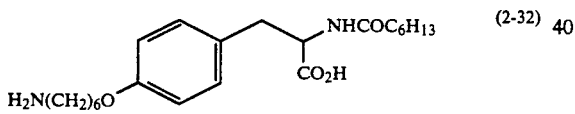
(2-32)

2-S-(Heptanoylamino)-3-[4-(6-aminohexyloxy)phenyl]-propionic acid hydrochloride (2-32)

2-31 (0.070 g) was dissolved in 30 mL EtOAc and treated with HCl gas as described for 2-2. Crude reaction product was triturated with 30 mL ether to provide pure 2-28 as a white solid.

$^1$H NMR (300 MHz, CD$_3$OD) δ0.88 (3H, t), 1.22 (6H, m), 1.47 (6H, m), 1.68 (2H, m), 1.78 (2H, m), 2.13 (2H, t), 2.80–2.95 (3H, m), 3.14 (1H, m), 3.30 (1H, m), 3.94 (2H, m), 4.61 (1H, m), 6.80 (2H, d), 7.13 (2H, d).

Analysis for C$_{22}$H$_{36}$N$_2$O$_4$.HCl.0.75H$_2$O Calc.: C=59.71, H=8.77, N=6.33. Found: C=59.76, H=8.40, N=6.25.

EXAMPLE 31(i)

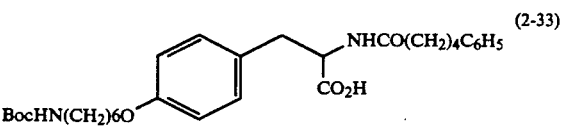
(2-33)

2-(S)-(5-PhenylpentanoylaminoO-3-[4-(6-N-t-butyloxycarbonylaminohexyloxy) phenyl]propionic acid (2-33)

2-1a (0.685 g, 1.8 mmole) was acylated with 5-phenylpentanoyl chloride as described for 2-15. Crude product was purified by flash chromatography on silica gel eluting with 96:3:1 CHCl$_3$/CH$_3$OH/HOAc to give pure 2-33 as a clear oil.

$^1$H NMR (300 MHz, CD$_3$OD) δ1.32–1.60 (1H, m), 1.73 (2H, m), 2.18 (2H, m), 2.53 (2H, m), 2.80–2.90 (1H, m), 3.02 (2H,t), 3.04 (1H, m), 4.62 (1H, m), 6.78 (2H, d), 7.08–7.28 (7H, m).

EXAMPLE 31(j)

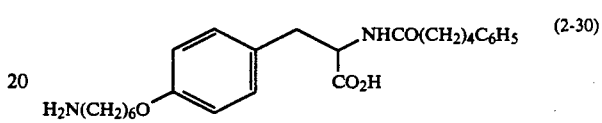
(2-30)

2-S-(5-Phenylpentanoylamino)-3-[4-(6-aminohexyloxy)-phenyl]propionic acid hydrochloride (2-34)

2-33 (0.49 g) was dissolved in 30 mL ethyl acetate and treated with HCl gas as described for 2-2. Crude product was triturated with 50 mL ether to give pure 2-34 (0.32 g) as a white solid.

$^1$H NMR (300 MHz, CD$_3$OD) δ1.40–1.58 (8H, m), 1.62–1.70 (2H, m), 1.80 (2H, m), 2.19 (2H, m), 2.55 (2H, m), 2.80–2.95 (3H, m), 3.15 (1H, m0, 3.30 (1H, m), 3.90 (2H, t), 4.62 (1H, m), 6.88 (2H, d), 7.08–7.27 (7H, m).

Analysis for C$_{26}$H$_{36}$N$_2$O$_4$.HCl.H$_2$O Calc.: C=64.24, H=7.88, N=5.76. Found: C=64.53, H=7.84, N=5.71.

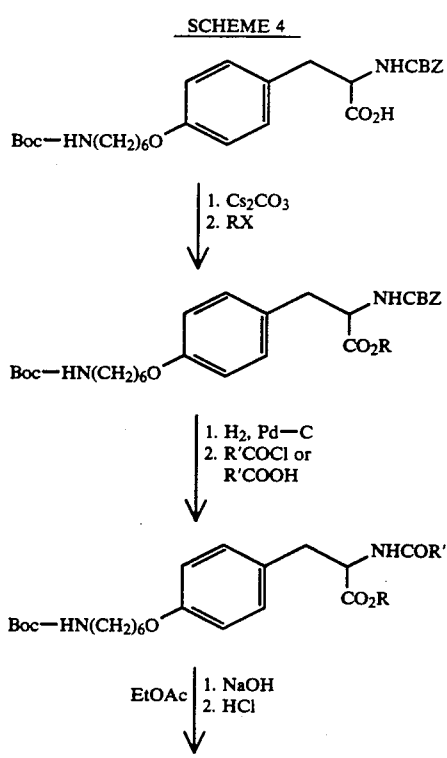

SCHEME 4

-continued
SCHEME 4

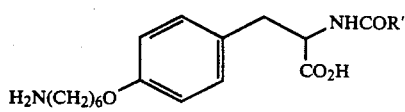

EXAMPLE 32

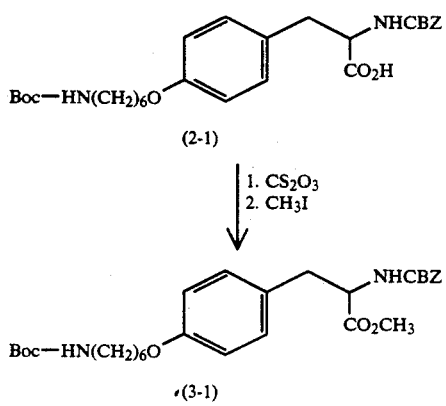

Methyl 2-S-(N-Benzyloxycarbonylamino)-3-[4-(6-N-t-butyloxycarbonylaminohexyl)oxyphenyl]propionate (3-1)

Compound 2-1 (10.0 g, 19.43 mmole) in 75 mL DMF was treated with cesium carbonate (3.16 g, 9.72 mmole) with stirring at room temperature for 1.9 hrs. Then, methyl iodide (2.76 g, 19.43 mmole) was added dropwise and the reaction mixture was stirred overnight at ambient temperature. The solvent was removed at high vacuum (30° C.) and the residue was taken up in 300 mL EtOAc and washed with 2×40 mL protions of saturated NaHCO$_3$ solution and brine and dried (Na$_2$SO$_4$). Solvent removal provided 3-1 as a clear oil.

$^1$H NMR (300 MHz, CDCl$_3$) δ1.25-1.53 (16H, m), 1.76 (2H, m), 2.96-3.17 (4H, m), 3.71 (3H, s), 3.90 (2H,t), 4.61 (1H, m), 5.10 (2H, m), 5.19 (1H, m), 6.88 (2H, d), 6.98 (2H, d), 7.32 (5H, m).

EXAMPLE 33

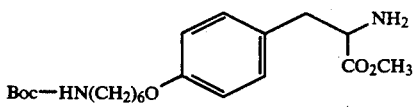

Methyl 2-S-Amino-3-[4-(6-N-t-butyloxycarbonylaminohexyloxy)phenyl]propionate (3-2)

Compound 3-1 (8.0 g, 15.1 mmole) was dissolved in 150 mL absolute ethanol and 1.0 g 10% Pd/C was added. This suspension was hydrogenated in a Parr apparatus (50 psi) for 3.5 hours. The catalyst was then filtered off and the solvent removed on the rotary evaporator to give pure 3-2 as a clear oil.

R$_f$=0.4 on SiO$_2$ with 95:5 CHCl$_3$/CH$_3$OH

1H NMR (300 MHz, CDCl$_3$) δ1.30–1.55 (16H, m), 1.70 (2H, m), 2.80 (1H, m), 3.00-3.17 (3H, m), 3.71 (3H, s), 3.93 (2H, t), 6.82 (2H, d), 7.09 (2H, d).

EXAMPLE 34

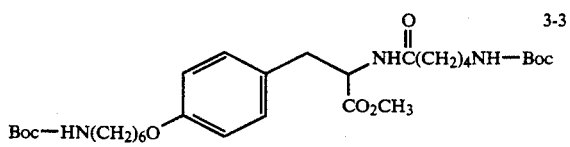

Methyl 2-S-[(5-N-t-Butyloxycarbonylamino)pentanoylamino]3-[4-(6-N-t-butyloxycarbonylaminohexyloxy)phenyl]propionate (3-3)

To a solution of 5-(N-t-butyloxycarbonylamino) pentanoic acid (0.293 g, 1.35 mmole) and N-methylmorpholine (0.187 g, 1.35 mmole) in 10 mL EtOAc at 0°–5° C. was added i-butylchloroformate (0.184 g, 1.35 mmole) via syringe and the resulting white suspension was stirred for 0.5 hours. Then, 3-2 (0.5 g, 1.27 mmole) dissolved in 10 mL EtOAc was added dropwise and the reaction mixture was stirred at 0° C. for 2.0 hours. The reaction mixture was then diluted with 25 mL water/40 mL EtOAc and the organic phase was separated, washed with water, 10% KHSO$_4$, water, saturated NaHCO$_3$, brine and dried (Na$_2$SO$_4$). Solvent removal gave an oil that was purified by flash chromatography on silica gel eluting with 2% CH$_3$OH/CHCl$_3$ (Rf=0.35) to give pure 3-3 as a clear oil.

$^1$H NMR (300 MHz, CDCl$_3$) δ1.35-1.55 (26H, m) 1.62 (2H, m), 1.68 (2H, m), 2.20 (2H, t), 3.0-3.16 (6H, m), 3.33 (3H, s), 3.92 (2H, t), 4.83 (1H, m), 6.80 (2H, d), 6.99 (2H, m).

EXAMPLE 35

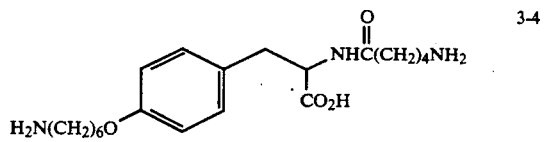

2-S-(5-Aminopentanoyl)amino-3-[4-(6-aminohexyloxy)-phenyl)]propionic acid dihydrochloride (3-4)

3-3 (0.68 g, 1.14 mmole) was dissolved in 30 mL THF(1)/MeOH(1)/H$_2$O(1), LiOH.H$_2$O (0.137 g, 5.73 mmole) was added and the reaction mixture stirred at room temperature overnight. The solvent was then removed and the residue was taken up 75 mL H$_2$O and acidified to pH 2-3 with 10% KHSO$_4$ solution. This was extracted with EtOAc and the combined organic extracts were washed with brine and dried (Na$_2$SO$_4$). Solvent removal gave 2-S-(5-N-t-butyloxycarbonylaminopentyl)amino-3-[4-(6-N-t-butyloxycarbonylaminohexyl)oxyphenyl]-propionic acid.

'H NMR (300 MHz, CDCl$_3$) δ1.40–.155 (22H, m). 1.60 (2H, m), 1.73 (2H, m), 2.20 (2H, m), 3.10 (4H, m), 3.90 (2H, m), 4.60 (1H, m), 4.72 (1H, m), 4.83 (1H, m), 6.78 (2H, d), 7.05 (2H, d).

This acid was dissolved in EtOAc and was treated with HCl gas as described for 2-2. The crude hydroscopic white solid was triturated with a solution of 10 mL EtOAc/50 mL Et$_2$O to give pure 3-4 as a white solid.

EXAMPLE 36

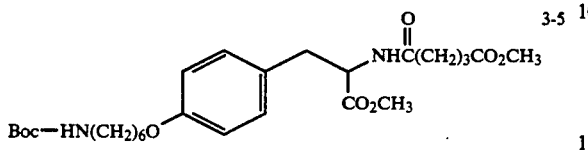

Methyl 2-S-[(4-Carbomethoxybutanoyl)amino]-3-[4-(N-t-butyloxycarbonylaminohexyloxy)-phenyl]propionate (3-5)

To a solution of 3-2 (0.5 g, 1.27 mmole), 4-carbomethoxybutanoic acid (0.213 g, 1.5 mmole) and 1 drop of triethylamine in 20 mL $CH_3CN$ was added BOP reagent (0.66 g, 1.5 mmole) and the resulting clear solution was stirred overnight at room temperature. The solvent was removed on the rotary evaporator and the residue was taken up in EtOAc and this was washed with $H_2O$, 10% $KHSO_4$, $H_2O$, saturated $NaHCO_3$, brine, and dried ($Na_2SO_4$). Solvent removal provided a residue that was purified by flash chromatography on silica gel eluting with 1% $CH_3OH/CHCl_3$ to give pure 3-5 as a clear oil.

$^1$H NMR (300 MHz, $CDCl_3$) δ1.35–1.55 (14H, m), 1.75 (3H, m), 1.94 (2H, m), 2.26 (2H, t), 2.35 (2H, t), 2.98–3.16 (4H, m), 3.67 (3H, s), 3.73 (3H, s), 3.91 (2H, t), 4.82 (1H, m), 6.80 (2H, d), 6.95 (2H, d).

EXAMPLE 37

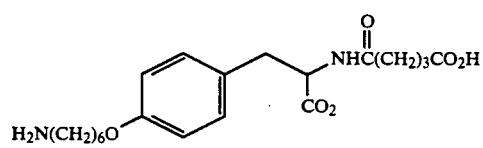

2-S-(4-Carboxybutanoylamino)-3-[4-(6-aminohexyloxy)phenyl]propionic acid (3-6)

3-5 (0.11 g, 0.21 mmole) was treated with LiOH (0.025 g, 1.05 mmole) as described for compound 3-4 to give the desired diacid.

$^1$H NMR (300 MHz, $CD_3OD$) δ1.30–1.55 (16H, m) 1.70–1.82 (4H, m), 2.20 (4H, m), 2.85 (1H, m), 3.03 (2H, m), 3.13 (1H, dd), 3.30 (1H, m), 3.92 (2H, m), 4.62 (1H, m), 6.81 (2H, d), 7.12 (2H, d).

This diacid (0.105 g) was dissolved in 30 mL EtOAc and treated with HCl gas as described for compound 2-2. The resulting solid was purified by flash chromatography on silica gel eluting with 90:8:8 ethanol/N-$H_4OH/H_2O$ to provide pure 3-6 as a white solid.

$^1$H NMR (300 MHz, $CD_3OD$) δ1.42 (2H, m), 1.50 (2H, m), 1.63 (2H, m), 1.76 (4H, m), 2.17 (4H, m), 2.85 (3H, m), 3.16 (1H, m), 4.0 (2H, t), 4.48 (1H, m), 6.78 (2H, d), 7.12 (2H, d).

Analysis for $C_{20}H_{30}N_2O_6 \cdot 1.2\ H_2O$. Calc.: C=57.73, H=7.85, N=6.73. Found: C=57.66, H=7.21, N=6.83.

$^1$H NMR (300 MHz $CD_3OD$) δ1.42–1.85 (14H, m), 2.23 (2H, m), 2.90 (6H, m), 3.14 (1H, dd), 3.30 (1H, m), 3.97 (2H,t), 4.60 (1H, m), 6.82 (2H, d), 7.13 (2H,d).

Analysis for $C_{20}H_{33}N_3O_4 \cdot 2HCl \cdot 3H_2O$. Calc.: C=47.43, H=8.16, N=8.30. Found: C=47.87, H=7.49, N=7.90.

EXAMPLE 38

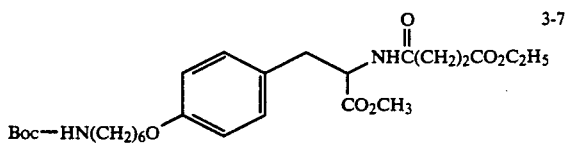

Methyl 2-S-[(3-Carboethoxypropanoyl)amino]-3-[4-(6-N-t-butyloxycarbonylaminohexyloxy)-phenyl]propionate (3-7)

3-2 (0.562 g, 1.42 mmole) was dissolved in 15 mL EtOAc and treated with $NaHCO_3$, (0.36 g, 4.27 mmole) and 3-carboethoxypropanoyl chloride (0.235 g, 1.42 mmole) with stirring overnight. The reaction mixture was diluted with 150 mL EtOAc and the organic phase was washed with $H_2O$, brine and dried ($Na_2SO_4$). Solvent removal gave a residue that was purified by flash chromatography on silica gel eluting with 98:2 $CHCl_3/CH_3OH$ to give pure 3-7.

$^1$H NMR (300 MHz, $CDCl_3$) δ1.26 (3H, t), 1.35–1.61 (16H, m), 1.76 (2H, m), 2.48 (2H, m), 2.63 (2H, m), 3.05 (2H, m), 3.11 (2H, m), 3.72 (3H, s), 3.92 (2H, t), 4.13 (2H, q), 4.82 (2H, m), 6.80 (2H, d), 7.00 (2H, d).

EXAMPLE 39

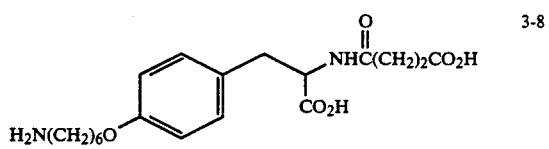

2-S-[(3-Carboxypropanoyl)amino]-3-[4-(6-aminohexyloxy)phenyl]propionic acid hydrochloride (3-8)

3-7 (0.58 g, 1.11 mmole) was treated with LiOH as described for 3-3 to give 2-S-[(3-carboxypropanoyl)amino-3-[4-(6-t-butyloxycarbonylaminohexyloxyphenyl]propionic acid as a foam.

$^1$H NMR (300 MHz $CH_3OD$) δ1.32–1.58 (16H, m), 1.77 (2H, m), 2.40 (4H, m), 2.89 (1H, m), 3.0–3.16 (3H, m), 3.33 (1H, m), 3.90 (2H, t), 4.42 (1H, m), 6.78 (2H, d), 7.11 (2H, d).

This acid (0.435 g) was treated with HCl gas in EtOAc (30 mL) as described for 2-2 to give a foam that was triturated with EtOAc to give pure 3-8 as a white solid.

$^1$H NMR (300 MHz, $CD_3OD$) δ1.4–1.6 (4H, m), 1.76 (2H, m), 2.46 (4H, m), 2.92 (3H, m), 3.14 (1H, m), 3.30 (1H, m), 3.96 (2H, m), 4.60 (1H, m), 6.81 (2H, d), 7.14 (2H, d).

Analysis for $C_{19}H_{28}N_2O_5 \cdot HCl \cdot 0.5\ H_2O$. Calc.: C=53.58, H=7.10, N=6.58. Found: C=53.18, H=6.93, N=6.27.

EXAMPLE 40

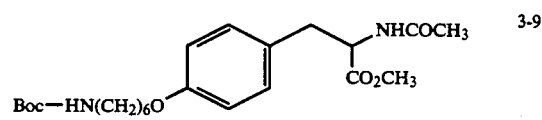

Methyl 2-S-(Acetylamino)-3-[4-(6-N-t-butyloxycarbonylaminohexyloxy)phenyl]propionate (3-9)

3-2 (0.562 g, 1.42 mmole) was treated with acetyl chloride (0.112 g, 4.27 mmole) as described for 3-7 to give a yellow oil. This was purified by flash chromatography on silica gel eluting with 98:2 CHCl$_3$/CH$_3$OH to give pure 3-9 as a clear oil.

$^1$H NMR (300 MHz, CDCl$_3$) δ1.30–1.56 (14H, m), 1.78 (2H, m), 2.00 (3H, s), 3.05–3.16 (4H, m), 3.73 (3H, s), 3.92 (2H, t), 4.84 (1H, m), 6.80 (2H, d), 6.98 (2H, d).

EXAMPLE 41

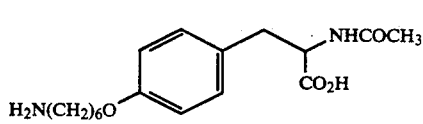

2-S-(Acetylamino)-3-[4-(6-aminohexyloxy)phenyl]propionic acid hydrochloride (3-10)

3-9 (0.58 g, 1.33 mmole) was treated with LiOH (0.16 g, 6.64 mmole) as described for 3-3 to give 2-S(acetylamino)-3-[4-(6-N-t-butyloxycarbonylaminohexyloxy)phenyl]propionic acid as a white solid.

$^1$H NMR (300 MHz, CD$_3$OD) δ1.35–1.53 (16H, m), 1.75 (2H,m), 1.90 (3H, s), 2.86 (1H, m), 3.00–3.15 (3H, m), 3.30 (1H, m), 3.93 (2H, t), 4.59 (1H, m), 6.82 (2H, d), 7.12 (2H, d).

This compound (0.485 g) was dissolved in 30 mL EtOAc and treated with HCl gas as described for 2-2 to give a residue that was triturated with EtOAc to provide pure 3-10 as a white solid.

$^1$H NMR (300 MHz, CD$_3$OD) δ1.42–1.60 (4H, m), 1.66 (2H, m), 1.70 (2H, m), 1.90 (3H, s), 2.82 (1H, m), 2.92 (2H, m), 3.12 (1H, dd), 3.30 (1H, m), 3.95 (2H, t), 4.60 (1H, m), 6.82 (2H, d), 7.13 (2H, d).

Analysis for C$_{17}$H$_{26}$N$_2$O$_4$·HCl·H$_2$O. Calc.: C=54.17, H=7.76, N=7.43. Found: C=54.30, H=7.71, N=7.09.

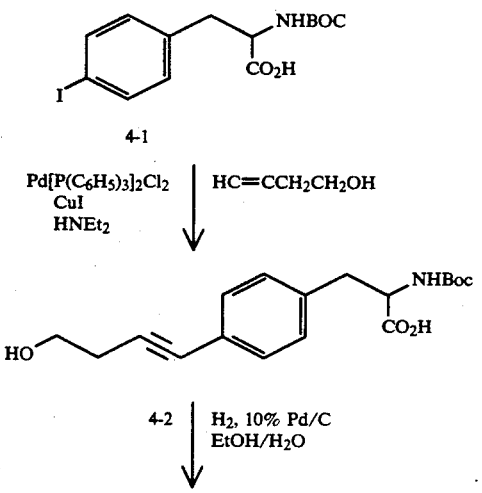

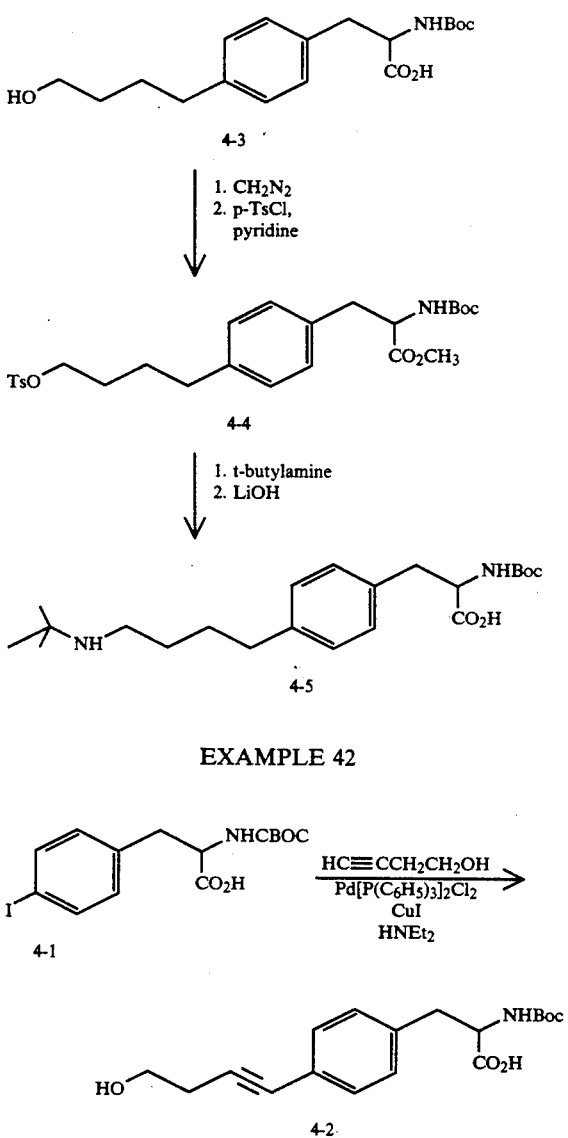

EXAMPLE 42

2-S-(N-t-Butyloxycarbonylamino)-3-[4-(4-hydroxybut-1-ynyl)-phenyl]propionic acid (4-2)

N-BOC-4-iodo-L-phenylalanine (4-1) (1.0 g, 2.55 mmole) was dissolved in diethylamine under N$_2$ and treated with 3-butyne-1-ol (0.23 mL, 3.06 mmole), Pd[PPh$_3$Cl$_2$ (0.089 g, 0.127 mmole) and CuI (0.012 g, 0.064 mmole). After 3 hours the solvent was evaporated, the residue dissolved in water (pH=11) and extracted with ethyl acetate. The water layer was then acidified to pH 3, extracted with ethyl acetate. This organic extract was dried and evaporated to give crude 4-2. R$_f$=0.47 in 97/3/1 CHCl$_3$/CH$_3$OH/HOAc, ninhydrin stain.

$^1$H NMR (300 MHz, CDCl$_3$) δ7.35 (2H, d), 7.1 (2H, d), 6.4 (1H, broad) 5.0 (1H, d), 4.6 (1H, m), 3.8 (2H, t), 3.1 (2H, m), 2.65 (2H, t), 1.4 (9H, s).

EXAMPLE 43

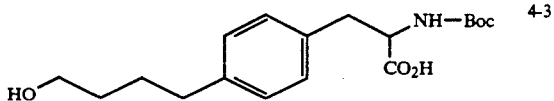

2-S-(N-t-Butyloxycarbonylamino)-3-[4-(4-hydroxybutyl)phenyl]propionic acid (4-3)

4-2 (0.40 g, 1.2 mmole) was dissolved in an ethanol/water solution (25 mL) and was treated with 10% Pd/C (0.1 g) and H$_2$ on a Parr apparatus. After 2 hours the solution was filtered and evaporated. Column chromatography on silica gel (94:5:1 CHCl$_3$/CH$_3$OH/HOAc) yielded 4-3. R$_f$=0.57 in 97:3:1 CHCl$_3$/CH$_3$OH/HOAc ninhydrin stain.

$^1$H NMR (300 MHz CDCl$_3$) δ7.1 (s, 4H), 4.95 (1H, m), 4.9 (1H, broad), 4.55 (1H, m), 3.65 (2H, t), 3.1 (2H, m), 1.6 (4H, m), 1.4 (9H, s).

EXAMPLE 44

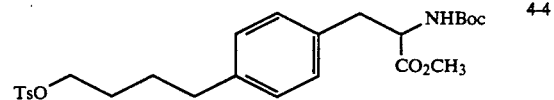

Methyl 2-S-(t-Butyloxycarbonylamino)-3-[4-(4-tosyloxybutyl)phenyl]propionate (4-4)

4-3 (0.285 g, 0.85 mmole) was dissolved in CH$_2$Cl$_2$ (10 mL) cooled to 0° C., and treated with CH$_2$N$_2$ solution. After 10 minutes the reaction was quenched with MgSO$_4$, filtered and evaporated to provide ester used in the next reaction. R$_f$=0.5 in 92:8:1 CHCl$_3$/CH$_3$OH/HOAc, ninhydrin stain.

$^1$H NMR (300 MHz, CDCl$_3$) δ7.05 (d, J=7.8 Hz, 2H), 7.0 (d,J=7.8 Hz, 2H), 5.0 (1H, m), 4.55 (1H, m), 3.69 (3H, s), 3.6 (2H, J=6.2 Hz, t), 3.0 (2H, m), 2.6 (2H, J=7.5 Hz, t), 1.7 (4H, m), 1.4 (9H, s).

This ester was dissolved in 10 mL CH$_2$Cl$_2$ and added at 78° C. to a solution prepared by treating p-toluenesulfonyl chloride (0.14 g, 0.67 mmole) in CH$_2$Cl$_2$ at −78° C. with pyridine (0.1 ml, 1.35 mmole) for 10 minutes. The reaction was allowed to warm to room temperature over 1.0 hour and then water was added. The organic layer was separated, dried, and evaporated. Column chromatography 97:3:1 CHCl$_3$/CH$_3$OH/HOAc gave 4-4. R$_f$=0.85 97:3:1 CHCl$_3$/CH$_3$OH/HOAc.

$^1$H NMR (300 MHz CDCl$_3$) δ7.88 (2H, J=7.2 Hz, d), 7.74 (2H, J=7.2 Hz, d), 7.38 (2H, J=Hz, d), 7.30 (2H, J=8 Hz, d), 5.0 (1H, m), 4.5 (1H, m), 4.0 (2H, J=5.3 Hz, t), 3.67 (3H, s), 3.0 (2H, m), 2.5 (2H, t), 2.0 (3H, s), 1.6 (4H, m), 1.4 (9H, s).

EXAMPLE 45

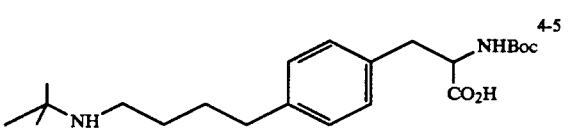

2-S-(N-t-Butyloxycarbonylamino)-3-[4-(4-t-butylaminobutyl)phenyl]propionic acid (4-5)

4-4 (0.26 g, 0.48 mmoles) was dissolved in t-butylamine (5 mL) and this solution was refluxed for 2 days. The reaction was filtered and the excess t-butylamine removed at high vacuum (30° C.). The residue was purified by flash chromatography on silica gel eluting with 98:2 CHCl$_3$ (saturated with NH$_3$)/CH$_3$OH to give methyl 2-S-(N-t-butyloxycarbonylamino)-3-[4-(4-t-butylaminobutyl)phenyl]propionate as an oil.

$^1$H NMR (300 MHz, CDCl$_3$) δ7.05 (2H, d), 7.0 (2H, d), 4.95 (1H, d), 4.55 (1H, m), 3.7 (3H, s), 3.0 (2H, m), 2.5 (2H, d), 1.80(4H, m), 1.40 (18H, s).

This ester (0.10 g, 2.7 mmole) was dissolved in 1:1:1 THF/CH$_3$OH/H$_2$O (10 mL) and LiOH.H$_2$O (0.033 g, 1.38 mmole) was added at room temperature. After stirring for 2 hours the solvent was removed and the residue chromatographed on silica gel eluting with 9:1:1 C$_2$H$_5$OH/H$_2$O/NH$_4$OH to give pure 4-5.

$^1$H NMR (300 MHz, D$_2$O) δ7.35 (4H, s), 4.25 (1H, dd), 3.2 (1H, m), 3.1 (2H, t), 2.9 (1H, m), 2.8 (2H, t), 1.8 (4H, m), 1.4 (18H, s).

Analysis for C$_{22}$H$_{36}$N$_2$O$_4$.1.0 CF$_2$CO$_2$H. Calc.: C=56.90, H=7.36, N=5.53. Found: C=56.73, H=7.51, N=5.58.

SCHEME 6

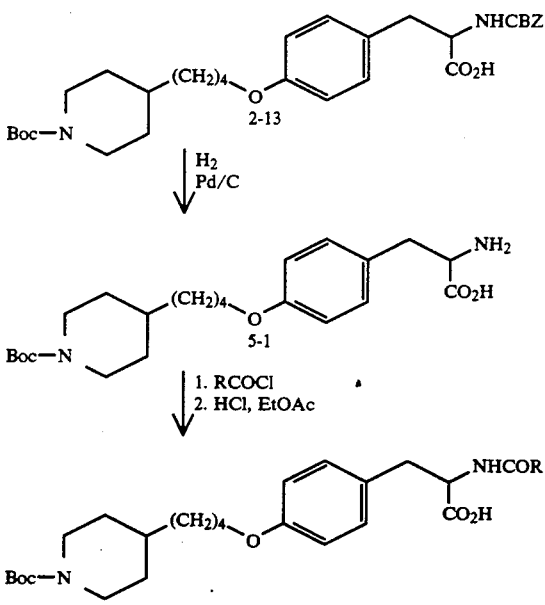

EXAMPLE 46

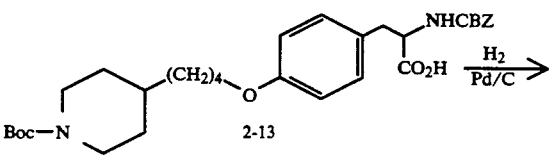

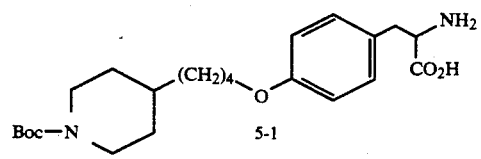

2-S-Amino-3-[4-(4-N-t-butyloxycarbonylpiperidin-4-yl)butyloxyphenyl]propionic acid (5-1)

2-13 (2.0 g) was dissolved in 100 mL EtOH, and 0.2 g 10% Pd/C was charged. This suspension was hydrogenated at balloon pressure overnight. Solvent removal provided 5-1 as a white solid.

$^1$H NMR (300 MHz, CD$_3$OD), δ0.97–1.12 (2H, m), 1.20–1.54 (14H, m), 1.72 (4H, m), 2.71 (2H, m), 2.90–3.00 (1H, m), 3.22 (1H, dd), 3.30 (1H, m), 3.71 (1H, m), 3.95–4.10 (4H, m), 6.88 (2H, d), 7.21 (2H, d).

EXAMPLE 47

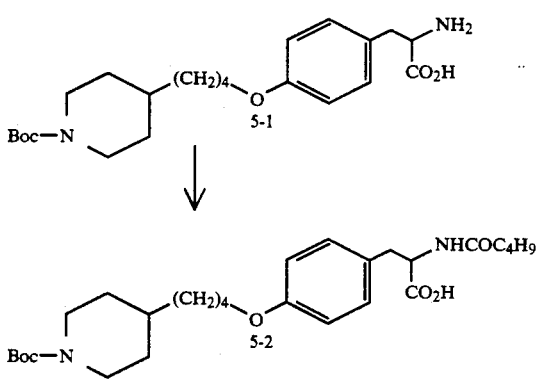

2-S-(Pentanoylamino)-3-[4-(4-N-t-butyloxycarbonyl-piperidin-4-yl)butyloxyphenyl]propanoic acid (5-2)

5-1 (1.05 g, 2.5 mmole) was added to a cold solution of 1 N NaOH (2.5 mL) in 20 mL H$_2$O and stirred at 0°–10° for 5 minutes to give a clear solution. Then, pentanoyl chloride (0.332 g, 2.75 mmole) was added dropwise followed by NaHCO$_3$ (0.231 g, 2.75 mmole) and the resulting mixture was stirred vigorously at 0°–10° for 1 hour. The reaction mixture was diluted with H$_2$O (75 mL), acidified to pH 2-3 with 10% KHSO$_4$ and extracted with EtOAc. This extract was filtered, washed with brine, dried (Na$_2$SO$_4$) and the solvent removed to give an oil. This was purified by flash chromatography on silica gel eluting with 97:3:1 CHCl$_3$/CH$_3$OH/HOAc to give pure 5-2 as a clear oil.

$^1$H NMR (300 MHz, CD$_3$OD) δ0.90 (3H, t), 1.20–1.62 (16H, m), 1.72 (2H, m), 2.14 (2H, m), 2.30 (8H, m), 2.65–2.90 (4H, m), 3.30 (1H, m), 3.93 (2H, m), 4.61 (1H, m), 6.81 (2H, d), 7.12 (2H, d).

EXAMPLE 48

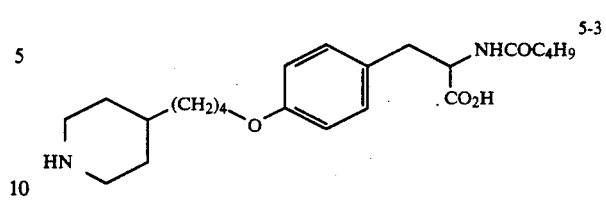

2-S-(Pentanoylamino)-3-[4-(4-piperidinylbutyloxy)-phenyl]propionic acid hydrochloride (5-3)

5-2 (0.449 g), was dissolved in 30 mL EtOAc and treated with HCl gas at −10° as described for 2-2. The resulting solid was triturated with 40 mL Et$_2$O to give pure 5-3 as a white solid.

$^1$H NMR (300 MHz, CD$_3$OD) δ0.85 (3H, t), 1.19 (2H, m), 1.30–1.65 (9H, m), 1.73 (2H, m), 1.95 (2H, m), 2.15 (2H, m), 2.80–3.02 (3H, m), 3.14 (1H, dd), 3.30–3.40 (3H, m), 3.95 (2H, t), 4.61 (1H, m), 6.82 (2H, d), 7.13 (2H, d).

Analysis for C$_{23}$H$_{36}$N$_2$O$_4$·HCl·0.75 H$_2$O. Calc.: C=60.77, H=8.54, N=6.16. Found: C=60.97, H=8.39, N=6.06.

EXAMPLE 49

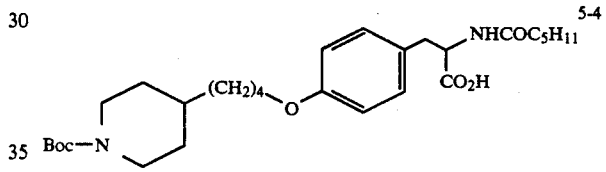

2-S-(Hexanoylamino)-3-[4-(4-N-t-butyloxycarbonyl-piperidin-4-yl)butyloxyphenyl]propionic acid (5-4)

5-1 (0.41 g) was treated with hexanoyl chloride (0.21 mL, 1.50 mmole) as described for 5-2. Crude product was purified by flash chromatography on silica gel eluting with 97:3:1 CHCl$_3$/CH$_3$OH/HOAc to give pure 5-4.

$^1$H NMR (300 MHz, CD$_3$OD) δ0.85 (3H, t), 0.97–1.35 (8H, M), 1.37–1.53 (12H, m), 1.60–1.80 (4H, m), 2.13 (2H, t), 2.80 (2H, m), 2.85 (1H, m), 3.12 (1H, dd) 3.90 (2H, t), 4.04 (2H, d), 4.62 (1H, m), 6.80 (2H, d), 7.12 (2H, d).

EXAMPLE 50

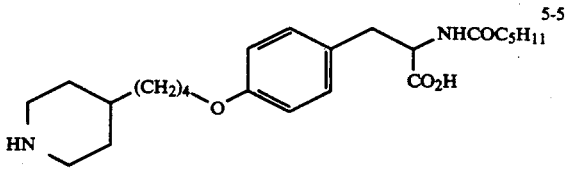

2-S-(Hexanoylamino)-3-[4-(4-piperidin-4-yl-butyloxy)-phenyl]propionic acid (5-5)

5-4 (0.199 g) was dissolved in 25 mL EtOAc and treated with HCl gas as described for compound 2-2 to provide pure 5-5.

$^1$H NMR (300 MHz, CD$_3$OD) δ0.84 (3H, t), 1.08–1.20 (4H, m), 1.35 (4H, m), 1.52 (4H, m), 1.77 (2H, m), 1.92 (2H, d), 2.16 (2H, t), 2.80-3.-2 (3H, m), 3.15 (1H, dd), 3.40-3.52 (2H, m), 3.92 (2H, t), 4.61 (1H, m), 6.81 (2H, d), 7.13 (2H, d).

Analysis for $C_{26}H_{39}N_2O_6F_3 \cdot 0.55\ H_2O \cdot 0.30$ TFA.

Calc.: C=55.39, H=7.06, N=4.86. Found: C=55.38, H=7.03, N=4.85.

Sample alternative protecting groups that can be used in the preparation of the present invention include benzyl ester, cyclohexyl ester, 4-nitrobenzyl ester, t-butyl ester, 4-pyridylmethyl ester, benzyloxycarbonyl, isonicotinyloxycarbonyl, O-chlorobenzyloxycarbonyl, p-nitrobenzyloxycarbonyl, p-methoxybenzyloxycarbonyl, t-butoxycarbonyl, t-amyl-oxycarbonyl, isobornyloxycarbonyl, adamantyloxycarbonyl, 2-(4-biphenyl)-2-propyloxycarbonyl and 9-fluorenylmethoxycarbonyl.

In addition to those compounds specifically exemplified above, additional compounds of the present invention are set forth in tabular form below. These compounds are synthesized by use of the synthetic routes and methods described in the above Schemes and Examples and variations thereof well known to those of ordinary skill in the art, and not requiring undue experimentation. All variables listed in the Tables below are with reference to the following generic structure:

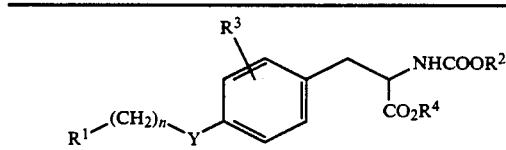

| n | $R^1$ | $R^2$ | $R^3$ | $R^4$ |
|---|---|---|---|---|
| 2 | (azabicyclic, N) | n-$C_4H_9$ | 2-$CH_3$ | H |
| 3 | (azetidinyl, HN) | t-$C_4H_9$ | H | $C_2H_5$ |
| 4 | $CH_3CH_2N$-pyrrolidinyl | i-$C_3H_7$ | 3-$C_2H_5$ | H |
| 5 | $PhCH_2N$-piperidinyl | n-$C_3H_7$ | H | t-Br |
| 6 | HN-N-H piperazinyl | $CH_2Ph$ | H | H |
| 5 | $CH_3N$-N- piperazinyl | t-$C_4H_9$ | 2-Ph | $CH_2Ph$ |
| 6 | O=HN-piperidinyl | $C_2H_5$ | H | H |

-continued

| n | $R^1$ | $R^2$ | $R^3$ | $R^4$ |
|---|---|---|---|---|
| 2 | (azabicyclic, N) | t-Bu | 3-$OCH_2CO_2H$ | $C_3H_7$ |
| 3 | $CH_3N$-N- piperazinyl with $CH_3$ | i-$C_3H_7$ | 2-F | H |
| 4 | tBu-N cyclohexyl | t-Bu | 3-$CH_3O$ | $C_2H_5$ |

The test procedures employed to measure the osteoclast inhibiting activity of the compounds used in the method of the present invention are described below.

EXAMPLE 51

When osteoclasts engage in bone resorption, they will literally cause the formation of pits in the surface of bone that they are acting upon. Therefore, when testing compounds for their ability to inhibit osteoclasts, it is useful to measure the ability of osteoclasts to excavate these resorption pits when the inhibiting compound is present.

Consecutive cross sections (4.4×4.4×0.2 mm) of bovine femur were cut from the diaphysis with a low-speed diamond saw (Isomet, Buehler, Ltd., Lake Bluff, Ill.) by the method of Arnett and Dempter. Endocrinology 120:602-608.

Prior to incubation with osteoclasts, slices were rehydrated in 0.1 ml complete medium 199 in a 48-well plate (Costar, Cambridge, Mass.) overnight in the presence of twice the desired dose of compound being tested.

Osteoclasts were isolated from the long bones of 1 to 3-day-old rats (Sprague-Dawley) by adaptations of methods used by Chambers, et al. J. Cell Sci. 66:383-399.

Femora, tibiae, and humeri were split and minced with scalpel blades into 2-5 ml Medium 199 (GIBCO, New York). The resulting suspension was gently pipetted (60 times with a wide-bore pipet and then aliquoted onto petri dishes (Costar) or bone slices (0.1 ml per slice). Cells were allowed to settle for 30-40 minutes at 37° C. in moist $CO_2$-air before gentle washing and reincubation in undiluted incubation medium. Osteoclast yields varied from 300 to 1400 per rat and typically comprised 1% or less of the total cell population.

Osteoclasts were counted at the day of isolation and after 1 day of incubation by phase-constrast microscopy (Nikon Diaphot). Total attached cells were counted 50-70 h after isolation with a Coulter counter (model ZM, Coulter Electronics, Inc., Hialeah, Fla.). Cell counts of controls varied from $3.352 \times 10^4$ to $2.322 \times 10^5$ per well. Counting mononuclear cells at the time of isolation was not practical because of matrix and cell debris that could not be completely eliminated.

Bone slices exposed to osteoclasts for 20 h after isolation were processed for staining by ultrasonication (twofold, 15 s, Branson) in 0.25 M ammonium hydroxide before fixation (20 minutes) in 2.5% glutaraldehyde, 0.1M cacodylate, pH 7.4 (EM Supplies, Fort Washington, Pa.). Samples were dehydrated in ethanol (40, 70, and 100%; 5 minutes), air dried for 2 h, and then stained for 4 minutes with filtered 1% toluidine blue and 1% borax (Sigma, St. Louis, Mo.). Samples used to count osteoclasts were processed as earlier without ultrasonication in ammonium hydroxide. Samples processed for scanning electron microscopy were not air dried but infiltrated for 40 minutes with 1:1 ethanol-Peldri II (Ted Pella, Inc., Redding, Calif.). After incubation in 100% Peldri II, solidified samples were exacuated overnight to sublimate the Peldri II. Slices were rotary shadowed with gold (DV-502A, Denton Vacuum, Cherry Hill, N.J.) and then examined on a JEOL JSM 840 at 3 kV accelerating voltage.

The morphology and motility of living osteoclasts were analyzed by recording phase-contrast images (Nikon, N.Y.) in real time onto 3/4 inch video-tapes with a u-matic VCR (Model VO 5800H, Sony).

A fluorescence microscope (Microphot, Nikon) was adapted for reflected light microscopy by inserting a $\lambda/4$ plate between cross polarizers in the epi mode. Fluorescence objectives of long working distance with adjustable correction collars ($10\times$, $20\times$, Nikon) were fitted with rotatable $\lambda/4$ plates (Polaroid Corp., Massachusetts) mounted as the front element. Correction collars were necessary $20\times$ objectives and higher to correct for the presence of the $\lambda/4$ plate and the absence of a coverslip. Coverslips were not used to eliminate stray reflections below the $\lambda/4$ plate. Immersion oil (Nikon) was added between the objective front lens and $\lambda/4$ plate to minimize reflections at this interface. Oil was not placed between objective and specimen.

Bone slices were scanned for resorption pits by rotating the $\lambda/4$ plate 0°–45° with respect to the plane of polarization in epi-tungsten illumination. Alternatively, Hg illumination (HBO 100 w, Nikon) was used with the $\lambda/4$ plate fixed at 45° while intermitently viewing stained images by transmission bright-field microscopy with an NCB 10 filter (Nikon).

Quantitation of resorbed areas of bone slices examined by bright-field, RLM, and SEM was achieved through digital image processing (Magiscan 2A, Joyce Loebl, New York) of video images (Newvicon or SIT, Dage-MTI, Inc. Michigan City, Ind.) fed through a NTSC/PAL digital standards converter (CEL P156, James Grunder and Assoc., Inc., Mission, Kans.).

Osteoclasts were processed for immunofluorescence by briefly rinsing coverslips in buffer S (60 mM Pipes, pH 6.9; 25 mM Hepes; 10 mM EGTA; and 2 mM $MgCl_2$) at 37° C. and then fixing for 2 minutes in buffer S+10% formaldehyde, pH 7.0. Cells were permeabilized in buffer S+0.5% Triton X-100 and then rinsed. Specimens were incubated (30 minutes) in appropriate antibody or rhodamine-phalloidine (Molecular probes, Eugene, Oreg.) followed by fluorescein goat antirabbit antibody (Cappel).

The bone slice assay is used to examine the effect of the compound of interest on the activity of isolated osteoclasts from rat long bones.

The number of resorption pits formed by osteoclasts after 1 day on consecutive cross sections of bovine femur was first compared to control samples by the method of Arnett and Dempster. Endocrinology 120:602–608, and then plotted as a function of concentration of the compound of interest. This is shown at FIG. 1.

The appropriateness of extrapolating data from this assay to utility and use in mammalian (including human) disease states is supported by the teaching found in Sato, M., et al., Journal of Bone and Mineral Research, Vol. 5, No. 1, 1990. That article teaches that certain bisphosphonates have been used clinically and appear to be effective in the treatment of Paget's disease, hypercalcemia of malignancy, osteolytic lesions produced by bone metastases, and bone loss due to immobilization or sex hormone deficiency. These same bisphosphonates are then tested in the resorption pit assay described above to confirm a correlation between their known utility and positive performance in the assay.

While the invention has been described and illustrated in reference to certain preferred embodiments thereof, those skilled in the art will appreciate that various changes, modifications and substitutions can be made therein without departing from the spirit and scope of the invention. For example, effective dosages other than the preferred doses as set forth hereinabove may be applicable as a consequence of variations in the responsiveness of the mammal being treated for severity of bone disorders caused by resorption, or for other indications for the compounds of the invention indicated above. Likewise, the specific pharmacological responses observed may vary according to and depending upon the particular active compound selected or whether there are present pharmaceutical carriers, as well as the type of formulation and mode of administration employed, and such expected variations or differences in the results are contemplated in accordance with the objects and practices of the present invention. It is intended, therefore, that the invention be limited only by the scope of the claims which follow and that such claims be interpreted as broadly as is reasonable.

What is claimed is:

1. A method of inhibiting the bone resorption activity of mammalian osteoclasts comprising the step of administering a pharmacologically effective amount of a compound of the formula

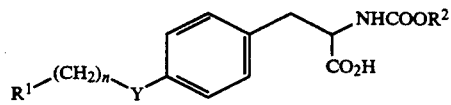

wherein
n is an integer of from 1 to 4;
Y is O;
$R^1$ is unsubstituted or substituted 5 or 6-membered saturated heterocyclic rings having 1 or 2 heteroatoms where said heteroatoms is N and said substituent is alkyl; and
$R^2$ is alkyl of 1 to 4 carbon atoms or benzyl.

2. The method as claimed in claim 1, in which said compound is

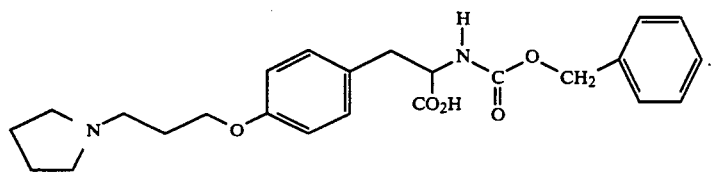
3. The method as claimed in claim 1, in which said compound is
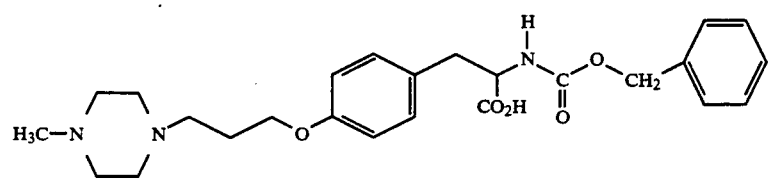
* * * * *